US009803010B2

(12) United States Patent
Reichert et al.

(10) Patent No.: US 9,803,010 B2
(45) Date of Patent: Oct. 31, 2017

(54) CRYSTALLINE ANTI-HUMAN IL-23P19 ANTIBODIES

(71) Applicant: Merck Sharp & Dohme Corp., Rahway, NJ (US)

(72) Inventors: Paul Reichert, Montville, NJ (US); Winifred W. Prosise, Ramsey, NJ (US); Peter Orth, New York, NY (US); Chakravarthy Nachu Narasimhan, Scotch Plains, NJ (US); Ramesh S. Kashi, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/407,319

(22) PCT Filed: Jun. 25, 2013

(86) PCT No.: PCT/US2013/047500
§ 371 (c)(1),
(2) Date: Dec. 11, 2014

(87) PCT Pub. No.: WO2014/004436
PCT Pub. Date: Jan. 3, 2014

(65) Prior Publication Data
US 2015/0147337 A1 May 28, 2015

Related U.S. Application Data

(60) Provisional application No. 61/665,172, filed on Jun. 27, 2012.

(51) Int. Cl.
*C07K 16/24* (2006.01)
*A61K 39/395* (2006.01)

(52) U.S. Cl.
CPC ...... *C07K 16/244* (2013.01); *A61K 39/39591* (2013.01); *C07K 2299/00* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,972,331 A | 10/1999 | Reichert et al. | |
| 6,902,734 B2 | 6/2005 | Giles-Komar et al. | |
| 6,914,128 B1 | 7/2005 | Salfeld et al. | |
| 7,166,285 B2 | 1/2007 | Giles-Komar et al. | |
| 7,247,711 B2 | 7/2007 | Benson et al. | |
| 7,491,391 B2 | 2/2009 | Benson et al. | |
| 7,504,485 B2 | 3/2009 | Salfeld et al. | |
| 7,615,213 B2 | 11/2009 | Kasaian et al. | |
| 7,833,525 B2 * | 11/2010 | Shenoy | A61K 9/0019 424/130.1 |
| 7,872,102 B2 | 1/2011 | Beidler et al. | |
| 7,935,344 B2 | 5/2011 | Benson et al. | |
| 7,998,477 B2 | 8/2011 | Yakovlevsky et al. | |
| 8,034,906 B2 | 10/2011 | Borhani et al. | |
| 8,168,760 B2 | 5/2012 | Borhani et al. | |
| 2007/0009526 A1 | 1/2007 | Benson et al. | |
| 2007/0048315 A1 | 3/2007 | Presta et al. | |
| 2009/0123479 A1 | 5/2009 | Bembridge et al. | |
| 2009/0311253 A1 | 12/2009 | Ghayur et al. | |
| 2010/0111966 A1 | 5/2010 | Presta et al. | |
| 2010/0272731 A1 | 10/2010 | Presta | |
| 2011/0040249 A1 * | 2/2011 | Benson | C07K 16/244 604/82 |

(Continued)

FOREIGN PATENT DOCUMENTS

| | | |
|---|---|---|
| EP | 1937721 | 7/2008 |
| EP | 1971366 | 9/2008 |

(Continued)

OTHER PUBLICATIONS

Aggarwal et al., "Interleukin-23 promotes a distinct CD4 T cell activation state characterized by the production of Interleukin-17," J. Biol. Chem. 278(3):1910-4 (Jan. 2003).
Baert et al., "Influence of immunogenicity on the long-term efficacy of infliximab in Crohn's disease," N. Engl. J. Med. 348(7):601-8 (Feb. 2003).
Beniaminovitz et al., "Prevention of rejection in cardiac transplantation by blockade of the interleukin-2 receptor with a monoclonal antibody," N. Engl. J. Med. 342(9):613-9 (Mar. 2000).
Bowman et al., "Rationale and safety of anti-interleukin-23 and anti-interleukin-17A therapy," Curr. Opin. Infect. Dis. 19(3):245-52 (Jun. 2006).

(Continued)

*Primary Examiner* — Elly-Gerald Stoica
(74) *Attorney, Agent, or Firm* — McDonnell Boehnen Hulbert & Berghoff LLP

(57) ABSTRACT

Crystalline forms of antibodies to human IL-23, such as antibodies to human IL-23p19, are provided, as well as methods of producing such crystalline forms, and uses of such crystalline forms, e.g. in treatment of inflammatory, autoimmune, and proliferative disorders. In various embodiments, the anti-huIL-23 antibody crystals, such as anti-huIL-23p19 antibody crystals of the present invention are obtainable by batch crystallization methods, vapor diffusion methods, liquid-liquid diffusion methods, and dialysis. In other aspects, the invention relates to suspensions of the crystalline anti-huIL-23 antibodies of the present invention, including those at higher concentrations and lower viscosities than would be possible with a corresponding non-crystalline solution at the same concentration of antibody. In other embodiments, the anti-huiL-23 antibody crystals of the present invention have increased stability, i.e. they maintain biological activity of the anti-huiL-23 antibody, such as anti-huiL-23p 19 antibody, longer than corresponding solution formulations.

8 Claims, 7 Drawing Sheets

(56) References Cited

U.S. PATENT DOCUMENTS

2013/0171128 A1* 7/2013 Huang .............. A61K 9/0019
424/130.1

FOREIGN PATENT DOCUMENTS

| WO | 00/53631 | 9/2000 | | |
|---|---|---|---|---|
| WO | 01/18051 | 3/2001 | | |
| WO | 02/072636 | 9/2002 | | |
| WO | 2004/071517 | 8/2004 | | |
| WO | 2004/081190 | 9/2004 | | |
| WO | 2005/040395 | 5/2005 | | |
| WO | 2005/121177 | 12/2005 | | |
| WO | 2007/024846 | 3/2007 | | |
| WO | 2007/076524 | 7/2007 | | |
| WO | 2007/147019 | 12/2007 | | |
| WO | 2008/057240 | 5/2008 | | |
| WO | 2008/103473 | 8/2008 | | |
| WO | WO2008103432 | * | 8/2008 | ............ C07K 16/24 |
| WO | 2008/106131 | 9/2008 | | |
| WO | 2008/121301 | 10/2008 | | |
| WO | 2008/134659 | 11/2008 | | |
| WO | 2008/153610 | 12/2008 | | |
| WO | 2009/020654 | 2/2009 | | |
| WO | 2009/082624 | 7/2009 | | |
| WO | 2009/123479 | 10/2009 | | |
| WO | 2010/017598 | 2/2010 | | |
| WO | 2010/115786 | 10/2010 | | |
| WO | 2011/056600 | 5/2011 | | |
| WO | 2011/109415 | 9/2011 | | |
| WO | 2012/009760 | 1/2012 | | |

OTHER PUBLICATIONS

Brange et al., "Insulin analogs with improved pharmacokinetic profiles," Adv. Drug Deliv. Rev. 35(2-3):307-35 (Feb. 1999).
Bruck et al., "Inflammation and degeneration in multiple sclerosis," Neurol. Sci. 24 Suppl 5:S265-7 (Dec. 2003).
Chang et al., "Premyelinating oligodendrocytes in chronic lesions of multiple sclerosis," N. Engl. J. Med. 346 (3):165-73 (Jan. 2002).
Chothia et al., "Canonical structures for the hypervariable regions of immunoglobulins," J. Mol. Biol. 196(4):901-17 (Aug. 1987).
Clarke et al., "A novel class of anti-IL-12p40 antibodies: potent neutralization via inhibition of IL-12-IL-12Rβ2 and IL-23-IL-23R," MAbs 2(5):539-49 (Sep. 2010).
Cua et al., "Interleukin-23 rather than interleukin-12 is the critical cytokine for autoimmune inflammation of the brain," Nature 421(6924):744-8 (Feb. 2003).
Davidson et al., "Autoimmune Diseases," N. Engl. J. Med. 345(5):340-50 (Aug. 2001).
Ding et al., "ABT-874, a fully human monoclonal anti-IL-12/IL-23 antibody for the potential treatment of autoimmune diseases," Curr. Opin. Investig. Drugs 9(5):515-22 (May 2008).
Dong "Diversification of T-helper-cell lineages: finding the family root of IL-17-producing cells," Nat. Rev. Immunol. 6(4):329-33 (Apr. 2006).
Elkins et al., "In vivo clearance of an intracellular bacterium, Francisella tularensis LVS, is dependent on the p40 subunit of interleukin-12 (IL-12) but not on IL-12 p70," Infect. Immun. 70(4):1936-48 (Apr. 2002).
Frucht, "IL-23: a cytokine that acts on memory T cells," Sci. STKE 2002(114):pe1-3 (Jan. 2002).
GenBank Accession No. NP_002178.
GenBank Accession No. NP_057668.
GenBank Accession No. P29460.
GeneID No. 51561.
Ghosh et al., "Natalizumab for active Crohn's disease," N. Engl. J. Med. 348(1):24-32 (Jan. 2003).
Giege et al., "Crystallogenesis of biological macromolecules: facts and perspectives," Acta Crystallogr. D Biol. Crystallogr. 50(Pt 4):339-50 (Jul. 1994).
Herold et al., "Anti-CD3 monoclonal antibody in new-onset type 1 diabetes mellitus," N. Engl. J. Med. 346 (22):1692-8 (May 2002).
Iwakura et al., "The IL-23/IL-17 axis in inflammation," J. Clin. Invest. 116(5):1218-22 (May 2006).
Jones, "On a New Substance Occurring in the Urine of a Patient with Mollities Ossium," Phil. Trans. R. Soc. Lond. 138:31-54 (1848).
Kenealy et al., "The genetic epidemiology of multiple sclerosis," J. Neuroimmunol. 143(1-2):7-12 (Oct. 2003).
Lipsky et al., "Infliximab and methotrexate in the treatment of rheumatoid arthritis. Anti-Tumor Necrosis Factor Trial in Rheumatoid Arthritis with Concomitant Therapy Study Group," N. Engl. J. Med. 343(22):1594-602 (Nov. 2000).
Liu et al., "Randomised, double blind, placebo controlled study of interferon beta-1a in relapsing-remitting multiple sclerosis analysed by area under disability/time curves," J. Neurol. Neurosurg. Psychiatry 67(4):451-6 (Oct. 1999).
McPherson et al., "Crystallization of proteins from polyethylene glycol," J. Biol. Chem. 251(20):6300-3 (Oct. 1976).
McPherson et al., "Current approaches to macromolecular crystallization," Eur. J. Biochem. 189(1):1-23 (Apr. 1990).
Milgrom et al., "Treatment of allergic asthma with monoclonal anti-IgE antibody. rhuMAb-E25 Study Group," N. Engl. J. Med. 341(26):1966-73 (Dec. 1999).
Miller et al., "A controlled trial of natalizumab for relapsing multiple sclerosis," N. Engl. J. Med. 348(1):15-23 (Jan. 2003).
Noseworthy et al., "Multiple sclerosis," N. Engl. J. Med. 343(13):938-52 (Sep. 2000).
Omim No. 605580.
Oppmann et al., "Novel p19 protein engages IL-12p40 to form a cytokine, IL-23, with biological activities similar as well as distinct from IL-12," Immunity 13(5):715-25 (Nov. 2000).
Parham et al., "A receptor for the heterodimeric cytokine IL-23 is composed of IL-12Rbeta1 and a novel cytokine receptor subunit, IL-23R," J. Immunol. 168(11):5699-708 (Jun. 2002).
Portielje et al., "IL-12: a promising adjuvant for cancer vaccination," Cancer Immunol. Immunother. 52(3):133-44 (Mar. 2003).
Slamon et al., "Use of chemotherapy plus a monoclonal antibody against HER2 for metastatic breast cancer that overexpresses HER2," N. Engl. J. Med. 344(11):783-92 (Mar. 2001).
Stumhofer et al., "Interleukin 27 negatively regulates the development of interleukin 17-producing T helper cells during chronic inflammation of the central nervous system," Nat. Immunol. 7(9):937-45 (Sep. 2006).
Tang et al., "Interleukin-23: as a drug target for autoimmune inflammatory diseases," Immunology 135(2):112-4 (Jan. 2012).
Tato et al., "Immunology: what does it mean to be just 17?," Nature 441(7090):166-8 (May 2006).
Veldhoen et al., "TGFbeta in the context of an inflammatory cytokine milieu supports de novo differentiation of IL-17-producing T cells," Immunity 24(2):179-89 (Feb. 2006).
Von Andrian et al., "T-cell function and migration. Two sides of the same coin," N. Engl. J. Med. 343(14):1020-34 (Oct. 2000).
Weber et al., "Physical principles of protein crystallization," Adv. Protein Chem. 41:1-36 (1991).
Wiekowski et al., "Ubiquitous transgenic expression of the IL-23 subunit p19 induces multiorgan inflammation, runting, infertility, and premature death," J. Immunol. 166(12):7563-70 (Jun. 2001).
Yang et al., "Crystalline monoclonal antibodies for subcutaneous delivery," Proc. Natl. Acad. Sci. U.S.A. 100 (12):6934-9 (Jun. 2003).
International Search Report for PCT Application No. PCT/US2013/047500; dated Aug. 18, 2014, pp. 1-6.
Supplementary European Search Report for EP Application No. EP13808570; dated Jan. 26, 2016, pp. 1-4.
FDA label of Entyvio, May 2014, pp. 1-21.
FDA label of Benlysta®, Mar. 2012, pp. 1-22.
FDA label of Xolair®, 2007, pp. 1-20.
FDA label of Blincyto®, Dec. 2014, pp. 1-24.
FDA label of Adcetris®, Nov. 2014, pp. 1-19.
FDA label of Ilaris, Mar. 2012, pp. 1-13.
FDA label of Raptiva®, Mar. 2009, pp. 1-36.
FDA label of Nucala®, Nov. 2015, pp. 1-28.

(56) References Cited

OTHER PUBLICATIONS

Krauss et al., "An Overview of Biological Macromolecule Crystallization" Int. J. Mol. Sci. 14: 11643-91 (2013).
Stura et al., "Crystallization of Antibodies and Antibody-Antigen Complexes," Immunomethods 3: 164-79 (1993).

* cited by examiner

SEQUENCE LISTING

```
<160> NUMBER OF SEQ ID NOS: 45

<210> SEQ ID NO 1
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Gly Phe Ala Tyr Trp Gly Gln Gly Thr Leu Val
            100                 105                 110
```

-continued

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 2
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 2

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Ile Phe Ile Thr Tyr
             20                  25                  30
Trp Met Thr Trp Val Arg Gln Ala Pro Gly Gln Gly Leu Glu Trp Met
         35                  40                  45
Gly Gln Ile Phe Pro Ala Ser Gly Ser Ala Asp Tyr Asn Glu Lys Phe
     50                  55                  60
Glu Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Gly Gly Gly Phe Ala Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
            435                 440                 445
```

<210> SEQ ID NO 3
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 3

```
Gln Val Gln Leu Val Gln Ser Gly Ala Glu Val Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
            35                  40                  45

Gly Gln Ile Phe Pro Ala Ser Gly Ser Ala Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 4
<211> LENGTH: 214
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(108)
<223> OTHER INFORMATION: Variable Domain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ile Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 5
<211> LENGTH: 10
<212> TYPE: PRT
<213> ORGANISM: Mus musculus

<400> SEQUENCE: 5

Gly Tyr Ile Phe Ile Thr Tyr Trp Met Thr
1               5                   10

<210> SEQ ID NO 6
<211> LENGTH: 17
<212> TYPE: PRT
<213> ORGANISM: Mus musculus

<400> SEQUENCE: 6

Gln Ile Phe Pro Ala Ser Gly Ser Ala Asp Tyr Asn Glu Met Phe Glu
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Rodent CDR with one amino acid substitution

<400> SEQUENCE: 7

Gln Ile Phe Pro Ala Ser Gly Ser Ala Asp Tyr Asn Glu Lys Phe Glu
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Rodent CDR with four amino acid substitutions

<400> SEQUENCE: 8

Gln Ile Phe Pro Ala Ser Gly Ser Ala Asp Tyr Ala Gln Lys Leu Gln
1               5                   10                  15

Gly

<210> SEQ ID NO 9
<211> LENGTH: 7
<212> TYPE: PRT
<213> ORGANISM: Mus musculus

<400> SEQUENCE: 9

Gly Gly Gly Gly Phe Ala Tyr
1               5

<210> SEQ ID NO 10
<211> LENGTH: 11
<212> TYPE: PRT
<213> ORGANISM: Mus musculus

<400> SEQUENCE: 10

Arg Thr Ser Glu Asn Ile Tyr Ser Tyr Leu Ala
1               5                   10

<210> SEQ ID NO 11
<211> LENGTH: 7
<212> TYPE: PRT
```

<213> ORGANISM: Mus musculus

<400> SEQUENCE: 11

Asn Ala Lys Thr Leu Ala Glu
1               5

<210> SEQ ID NO 12
<211> LENGTH: 9
<212> TYPE: PRT
<213> ORGANISM: Mus musculus

<400> SEQUENCE: 12

Gln His His Tyr Gly Ile Pro Phe Thr
1               5

<210> SEQ ID NO 13
<211> LENGTH: 170
<212> TYPE: PRT
<213> ORGANISM: Homo sapiens

<400> SEQUENCE: 13

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Thr Thr Asn Asp
        35                  40                  45

Val Pro His Ile Gln Cys Gly Asp Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 14
<211> LENGTH: 1398
<212> TYPE: DNA
<213> ORGANISM: Artificial Sequence
<220> FEATURE:
<223> OTHER INFORMATION: Human constant and framework regions, rodent
      CDRs

<400> SEQUENCE: 14
atggctgtgc tggggctgct gttctgcctg gtgacattcc caagctgtgt gctgtcccag    60
gtgcagctgg tgcagtctgg cgctgaggtg aagaagcctg gcgcctccgt gaaggtctcc   120
tgcaaggctt ctggctacat cttcatcacc tactggatga cctgggtgcg gcaggcccct   180
ggccaggggc tggagtggat gggccagatc ttccctgcca gcggctctgc agactacaac   240
gagaagttcg aaggcagagt caccatgacc acagacacat ccaccagcac agcctacatg   300

```
gagctgagga gcctgagatc tgacgacacc gccgtgtatt actgtgccag aggcggtggc      360
ggattcgctt actggggcca gggcaccctg gtcaccgtct ccagcgctag caccaagggc      420
ccatcggtct tccccctggc accctcctcc aagagcacct ctgggggcac agcggccctg      480
ggctgcctgg tcaaggacta cttccccgaa ccggtgacgg tgtcgtggaa ctcaggcgcc      540
ctgaccagcg gcgtgcacac cttcccggct gtcctacagt cctcaggact ctactccctc      600
agcagcgtgg tgaccgtgcc ctccagcagc ttgggcaccc agacctacat ctgcaacgtg      660
aatcacaagc ccagcaacac caaggtggac aagaaagttg agcccaaatc ttgtgacaaa      720
actcacacat gcccaccgtg cccagcacct gaactcctgg ggggaccgtc agtcttcctc      780
ttccccccaa aacccaagga caccctcatg atctcccgga cccctgaggt cacatgcgtg      840
gtggtggacg tgagccacga agaccctgag gtcaagttca actggtacgt ggacggcgtg      900
gaggtgcata atgccaagac aaagccgcgg gaggagcagt acaacagcac gtaccgtgtg      960
gtcagcgtcc tcaccgtcct gcaccaggac tggctgaatg gcaaggagta caagtgcaag     1020
gtctccaaca aagccctccc agcccccatc gagaaaacca tctccaaagc caaagggcag     1080
ccccgagaac cacaggtgta caccctgccc ccatcccggg atgagctgac caagaaccag     1140
gtcagcctga cctgcctggt caaaggcttc tatcccagcg acatcgccgt ggagtgggag     1200
agcaatgggc agccggagaa caactacaag accacgcctc ccgtgctgga ctccgacggc     1260
tccttcttcc tctacagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaatga                                                   1398

<210> SEQ ID NO 15
<211> LENGTH: 702
<212> TYPE: DNA
<213> ORGANISM: Artificial Sequence
<220> FEATURE:
<223> OTHER INFORMATION: Human constant and framework regions, rodent
      CDRs

<400> SEQUENCE: 15
atggctccag tgcagctgct ggggctgctg gtgctgttcc tgccagccat gagatgtgat       60
atccagatga cccagtctcc atcctccctg tctgcctctg tgggcgacag agtgaccatc      120
acctgcagga ccagcgagaa catctacagc tacctggcct ggtatcagca gaagccaggg      180
aaggccccta gctgctgat ctataacgcc aagaccctgg ctgaagggt gccatccagg      240 ttcagcggca gcggctctgg gacagacttc accctgacca tcagcagcct gcagcctgag      300
gacttcgcca cctactactg tcagcaccac tacggaattc cattcacctt cggccagggc      360
accaaggtgg agatcaagcg tacggtggct gcaccatctg tcttcatctt ccctccatct      420
gatgagcagc tgaagtctgg aactgcctcc gtggtgtgcc tgctgaataa cttctatccc      480
agagaggcca aggtgcagtg gaaggtggat aacgccctcc agagcggcaa ctcccaggag      540
agcgtgacag agcaggacag caaggacagc acctacagcc tgagcagcac cctgaccctg      600
agcaaagcag actacgagaa acacaaggtg tacgcctgcg aggtgaccca tcagggcctg      660
agcagccccg tgacaaagag cttcaacagg ggagagtgtt aa                        702

<210> SEQ ID NO 16
<211> LENGTH: 5
<212> TYPE: PRT
<213> ORGANISM: Homo sapiens
```

```
<400> SEQUENCE: 16

Thr Tyr Trp Leu Gly
1               5

<210> SEQ ID NO 17
<211> LENGTH: 16
<212> TYPE: PRT
<213> ORGANISM: Homo sapiens

<400> SEQUENCE: 17

Ile Met Ser Pro Val Asp Ser Asp Ile Arg Tyr Ser Pro Ser Phe Gln
1               5                   10                  15

<210> SEQ ID NO 18
<211> LENGTH: 10
<212> TYPE: PRT
<213> ORGANISM: Homo sapiens

<400> SEQUENCE: 18

Arg Arg Pro Gly Gln Gly Tyr Phe Asp Phe
1               5                   10

<210> SEQ ID NO 19
<211> LENGTH: 11
<212> TYPE: PRT
<213> ORGANISM: Homo sapiens

<400> SEQUENCE: 19

Arg Ala Ser Gln Gly Ile Ser Ser Trp Leu Ala
1               5                   10

<210> SEQ ID NO 20
<211> LENGTH: 7
<212> TYPE: PRT
<213> ORGANISM: Homo sapiens

<400> SEQUENCE: 20

Ala Ala Ser Ser Leu Gln Ser
1               5

<210> SEQ ID NO 21
<211> LENGTH: 9
<212> TYPE: PRT
<213> ORGANISM: Homo sapiens

<400> SEQUENCE: 21

Gln Gln Tyr Asn Ile Tyr Pro Tyr Thr
1               5

<210> SEQ ID NO 22
<211> LENGTH: 119
<212> TYPE: PRT
<213> ORGANISM: Homo sapiens

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
                20                  25                  30

Trp Leu Gly Trp Val Arg Gln Met Pro Gly Lys Gly Leu Asp Trp Ile
            35                  40                  45

Gly Ile Met Ser Pro Val Asp Ser Asp Ile Arg Tyr Ser Pro Ser Phe
```

```
                50                  55                  60
Gln Gly Gln Val Thr Met Ser Val Asp Lys Ser Ile Thr Thr Ala Tyr
 65                  70                  75                  80

Leu Gln Trp Asn Ser Leu Lys Ala Ser Asp Thr Ala Met Tyr Tyr Cys
                 85                  90                  95

Ala Arg Arg Arg Pro Gly Gln Gly Tyr Phe Asp Phe Trp Gly Gln Gly
            100                 105                 110

Thr Leu Val Thr Val Ser Ser
        115

<210> SEQ ID NO 23
<211> LENGTH: 108
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Tyr
                 85                  90                  95

Thr Phe Gly Gln Gly Thr Lys Leu Glu Ile Lys Arg
            100                 105

<210> SEQ ID NO 24
<211> LENGTH: 449
<212> TYPE: PRT
<213> ORGANISM: Homo sapiens

<400> SEQUENCE: 24

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Thr Tyr
             20                  25                  30

Trp Leu Gly Trp Val Arg Gln Met Pro Gly Lys Gly Leu Asp Trp Ile
         35                  40                  45

Gly Ile Met Ser Pro Val Asp Ser Asp Ile Arg Tyr Ser Pro Ser Phe
     50                  55                  60

Gln Gly Gln Val Thr Met Ser Val Asp Lys Ser Ile Thr Thr Ala Tyr
 65                  70                  75                  80

Leu Gln Trp Asn Ser Leu Lys Ala Ser Asp Thr Ala Met Tyr Tyr Cys
                 85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
```

```
            145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 25
<211> LENGTH: 214
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Asn Ile Tyr Pro Tyr
                    85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 26
<211> LENGTH: 9
<212> TYPE: PRT
<213> ORGANISM: Homo sapiens

<400> SEQUENCE: 26

Phe Thr Phe Ser Ser Tyr Gly Met His
1               5

<210> SEQ ID NO 27
<211> LENGTH: 17
<212> TYPE: PRT
<213> ORGANISM: Homo sapiens

<400> SEQUENCE: 27

Phe Ile Arg Tyr Asp Gly Ser Asn Lys Tyr Tyr Ala Asp Ser Val Lys
1               5                   10                  15

Gly

<210> SEQ ID NO 28
<211> LENGTH: 6
<212> TYPE: PRT
<213> ORGANISM: Homo sapiens

<400> SEQUENCE: 28

His Gly Ser His Asp Asn
1               5

<210> SEQ ID NO 29
<211> LENGTH: 13
<212> TYPE: PRT
<213> ORGANISM: Homo sapiens

<400> SEQUENCE: 29

Ser Gly Ser Arg Ser Asn Ile Gly Ser Asn Thr Val Lys
1               5                   10

<210> SEQ ID NO 30
<211> LENGTH: 7
<212> TYPE: PRT
```

```
<213> ORGANISM: Homo sapiens

<400> SEQUENCE: 30

Tyr Asn Asp Gln Arg Pro Ser
1               5

<210> SEQ ID NO 31
<211> LENGTH: 12
<212> TYPE: PRT
<213> ORGANISM: Homo sapiens

<400> SEQUENCE: 31

Gln Ser Tyr Asp Arg Tyr Thr His Pro Ala Leu Leu
1               5                   10

<210> SEQ ID NO 32
<211> LENGTH: 115
<212> TYPE: PRT
<213> ORGANISM: Homo sapiens

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 33
<211> LENGTH: 112
<212> TYPE: PRT
<213> ORGANISM: Homo sapiens

<400> SEQUENCE: 33

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Tyr Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110
```

<210> SEQ ID NO 34
<211> LENGTH: 445
<212> TYPE: PRT
<213> ORGANISM: Homo sapiens

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 35
<211> LENGTH: 217
<212> TYPE: PRT
<213> ORGANISM: Homo sapiens

<400> SEQUENCE: 35

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 36
<211> LENGTH: 5
<212> TYPE: PRT
<213> ORGANISM: Homo sapiens

<400> SEQUENCE: 36

Asn Tyr Trp Ile Gly
1               5

<210> SEQ ID NO 37
<211> LENGTH: 17
<212> TYPE: PRT
<213> ORGANISM: Homo sapiens

<400> SEQUENCE: 37

Ile Ile Asp Pro Ser Asn Ser Tyr Thr Arg Tyr Ser Pro Ser Phe Gln
1               5                   10                  15

Gly

<210> SEQ ID NO 38
<211> LENGTH: 8
<212> TYPE: PRT
<213> ORGANISM: Homo sapiens

<400> SEQUENCE: 38

Trp Tyr Tyr Lys Pro Phe Asp Val
1               5

<210> SEQ ID NO 39
<211> LENGTH: 14
<212> TYPE: PRT
<213> ORGANISM: Homo sapiens

<400> SEQUENCE: 39

Thr Gly Ser Ser Ser Asn Ile Gly Ser Gly Tyr Asp Val His
1               5                   10

<210> SEQ ID NO 40
<211> LENGTH: 7
<212> TYPE: PRT
<213> ORGANISM: Homo sapiens

<400> SEQUENCE: 40

Gly Asn Ser Lys Arg Pro Ser
1               5

<210> SEQ ID NO 41
<211> LENGTH: 11
<212> TYPE: PRT
<213> ORGANISM: Homo sapiens

<400> SEQUENCE: 41

Ala Ser Trp Thr Asp Gly Leu Ser Leu Val Val
1               5                   10

<210> SEQ ID NO 42
<211> LENGTH: 117
<212> TYPE: PRT
<213> ORGANISM: Homo sapiens

<400> SEQUENCE: 42

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu

```
                    100                 105                 110

Val Thr Val Ser Ser
            115

<210> SEQ ID NO 43
<211> LENGTH: 111
<212> TYPE: PRT
<213> ORGANISM: Homo sapiens

<400> SEQUENCE: 43

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 44
<211> LENGTH: 446
<212> TYPE: PRT
<213> ORGANISM: Homo sapiens

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
                195                 200                 205
Thr Lys Val Asp Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
            435                 440                 445

<210> SEQ ID NO 45
<211> LENGTH: 217
<212> TYPE: PRT
<213> ORGANISM: Homo sapiens

<400> SEQUENCE: 45

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ser Gly
                20                  25                  30
Tyr Asp Val His Trp Tyr Gln Gln Leu Pro Gly Thr Ala Pro Lys Leu
            35                  40                  45
Leu Ile Tyr Gly Asn Ser Lys Arg Pro Ser Gly Val Pro Asp Arg Phe
        50                  55                  60
Ser Gly Ser Lys Ser Gly Thr Ser Ala Ser Leu Ala Ile Thr Gly Leu
65                  70                  75                  80
Gln Ser Glu Asp Glu Ala Asp Tyr Tyr Cys Ala Ser Trp Thr Asp Gly
                85                  90                  95
Leu Ser Leu Val Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
```

-continued

```
Glu Leu Gln Ala Asn Lys Ala Thr Leu Val Cys Leu Ile Ser Asp Phe
    130             135                 140

Tyr Pro Gly Ala Val Thr Val Ala Trp Lys Ala Asp Ser Ser Pro Val
145             150             155                     160

Lys Ala Gly Val Glu Thr Thr Thr Pro Ser Lys Gln Ser Asn Asn Lys
                165             170                 175

Tyr Ala Ala Ser Ser Tyr Leu Ser Leu Thr Pro Glu Gln Trp Lys Ser
            180             185                 190

His Arg Ser Tyr Ser Cys Gln Val Thr His Glu Gly Ser Thr Val Glu
        195             200             205

Lys Thr Val Ala Pro Thr Glu Cys Ser
    210             215
```

CRYSTALLINE ANTI-HUMAN IL-23P19 ANTIBODIES

FIELD OF THE INVENTION

The present invention relates generally to crystalline forms of antibodies specific for human interleukin-23 and uses thereof. More specifically, the invention relates to crystalline forms of antibodies that recognize human IL-23p19 and modulate its activity, particularly in inflammatory, autoimmune and proliferative disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Interleukin-12 (IL-12) is a heterodimeric molecule composed of p35 and p40 subunits. Studies have indicated that IL-12 plays a critical role in the differentiation of naïve T cells into T-helper type 1 CD4$^+$ lymphocytes that secrete IFNγ. It has also been shown that IL-12 is essential for T cell dependent immune and inflammatory responses in vivo. See, e.g., Cua et al. (2003) *Nature* 421:744-748. The IL-12 receptor is composed of IL-12Rβ1 and IL-12Rβ2 subunits.

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12Rβ1, which is shared by the IL-12 receptor. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23 (see, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948).

Recent studies, through the use of p40 KO mice, have shown that blockade of both IL-23 and IL-12 is an effective treatment for various inflammatory and autoimmune disorders. However, the blockade of IL-12 through p40 appears to have various systemic consequences such as increased susceptibility to opportunistic microbial infections. Bowman et al. (2006) *Curr. Opin. Infect. Dis.* 19:245.

Therapeutic antibodies may be used to block cytokine activity. Subcutaneous administration is the preferred method of administration of many such antibodies, at least in part because it enables self-administration. Therapeutic antibodies are traditionally prepared in lyophilized form or in solution. Lyophilized forms may exhibit enhanced long-term stability, but require reconstitution prior to use, making them less than ideal for self-administration. Solution formulations do not require reconstitution, but may suffer from reduced stability and typically require cold storage prior to use. Both lyophilized and solution formulations may fail to provide sufficiently high concentrations to allow for high dose delivery by subcutaneous administration. High concentration solution formulations, if achievable, may also be prone to dropping out of solution, or may be too viscous to be delivered in a narrow gauge needle, e.g. as required for subcutaneous administration, particularly self-administration.

Exemplary engineered antibodies to IL-23p19 are disclosed in commonly-assigned U.S. Patent Application Publication Nos. 2010/0272731 and 2010/0111966, in U.S. Patent Application Publication Nos. 2007/0009526 and 2007/0048315, and in International Patent Publication Nos. WO 2007/076524, WO 2007/024846 and WO 2007/147019. One IL-23 antagonist antibody, ustekinumab (STELARA®), is commercially available, but it binds to the p40 subunit of IL-23 rather than the p19 subunit. As a result, ustekinumab also inhibits the activity of IL-12, which is generally an undesired side effect that can lead to increased susceptibility of certain infections and tumors. Bowman et al. (2006) *Curr. Opin. Infect. Dis.* 19:245. Briakinumab, another anti-p40 antibody that has entered clinical trials, suffers from the same safety concerns. Anti-human IL-23p19 antibody guselkumab (CNTO-1959) has entered clinical trials.

The need exists for improved formulations of anti-huIL-23p19 antibodies for use, e.g., in treatment of inflammatory, autoimmune, and proliferative disorders. Preferably, such antibody formulations will not require reconstitution prior to administration. In addition, such formulations will enable higher concentration administration of the antibody than would be readily achievable using typical solution formulations, and will preferably support high concentrations with sufficiently low viscosity to be conveniently delivered subcutaneously. Such formulations may also provide for sustained release, and will also be more stable than typical solution formulations.

SUMMARY OF THE INVENTION

The present invention satisfies these needs and more by providing crystalline forms of anti-huIL-23 antibodies, such as antibodies that bind to the p19 subunit of human IL-23 (anti-human IL-23p19 antibodies). In one aspect, the invention relates to crystalline forms of anti-huIL-23 antibodies, such as anti-huIL-23p19 antibodies. In another aspect, the invention relates to suspensions of these crystalline forms of anti-huIL-23 antibodies, such as anti-huIL-23p19 antibodies, e.g. as crystalline slurries. In yet another aspect, the invention relates to pharmaceutical formulations comprising suspensions of these crystalline forms of anti-huIL-23 antibodies, such as anti-huIL-23p19 antibodies. In various embodiments, the crystalline form of the anti-huIL-23 antibodies, such as anti-huIL-23p19 antibodies, is used to facilitate purification, storage, and therapeutic administration of the anti-huIL-23 antibody.

In some embodiments, the anti-huIL-23 antibody crystals, such as anti-huIL-23p19 antibody crystals, of the present invention have an average particle size between five and 200 microns. In other embodiments, the anti-huIL-23 antibody crystals, such as anti-huIL-23p19 antibody crystals, are characterized by unit cell dimensions of a=b=192 Å, c=106 Å, α=β=γ=90° and are in space group I4. In some embodiments, the anti-huIL-23p19 antibody crystals can diffract X-rays to a resolution of at least about 5 Å.

In various embodiments, the anti-huIL-23 antibody crystals, such as anti-huIL-23p19 antibody crystals, of the present invention are obtainable by batch crystallization methods, vapor diffusion methods, liquid-liquid diffusion methods, and dialysis.

In other aspects, the invention relates to suspensions of the crystalline anti-huIL-23 antibodies, such as anti-human IL-23p19 antibodies, of the present invention, including those at higher concentrations and lower viscosities than would be possible with a corresponding non-crystalline solution at the same concentration of antibody. In some embodiments the crystalline suspension of anti-huIL-23 antibody crystals, such as anti-huIL-23p19 antibody crystals, has an antibody concentration of greater than about 50, 100, 150, 200 or 250 mg/ml. In one aspect, the invention relates to suspensions of crystalline anti-human IL-23p19 antibodies that are substantially less viscous than a corresponding non-crystalline solution at the same concentration of antibody. In one embodiment the suspension has a viscosity of less than half that of a corresponding solution formulation, and has an antibody concentration of at least about 150 or 200 mg/ml.

In other embodiments, the anti-huIL-23 antibody crystals, such as anti-huIL-23p19 antibody crystals, of the present invention have increased stability, i.e. they maintain biological activity of the anti-huIL-23 antibody, such as anti-huIL-23p19 antibody, longer than corresponding solution formulations. In some embodiments, the increased stability is at room temperature, enabling storage of the crystalline suspensions of the present invention at room temperature rather than at 4° C., such as room temperature (e.g. 20° C.-25° C.).

In some embodiments, the anti-huIL-23 antibody comprises the CDR sequences of ustekinumab or briakinumab. In various other embodiments, the anti-huIL-23p19 antibody comprises the CDR sequences of antibodies 13B8-a, 13B8-b or 13B8-c of commonly assigned Intl Pat. App. Pub. WO 08/103432, or the CDR sequences of antibodies LY2525623 or CNTO 1959 (guselkumab).

In a preferred embodiment, the crystalline anti-huIL-23p19 antibody comprises a light chain variable domain in which CDRL1 comprises the sequence of SEQ ID NO: 10; CDRL2 comprises the sequence of SEQ ID NO: 11; and CDRL3 comprises the sequence of SEQ ID NO: 12, and a heavy chain variable domain in which CDRH1 comprises the sequence of SEQ ID NO: 5; CDRH2 comprises a sequence selected from the group consisting of SEQ ID NOs: 6-8; and CDRH3 comprises the sequence of SEQ ID NO: 9. In a preferred refinement of the preceding embodiment, CDRH2 comprises the sequence of SEQ ID NO: 7.

In a further embodiment the crystalline anti-huIL-23p19 antibody comprises the light chain variable domain (residues 1-108) of SEQ ID NO: 4 and a heavy chain variable domain (residues 1-116) of a sequence selected from the group consisting of SEQ ID NOs: 1-3. In a preferred refinement of the preceding embodiment, the heavy chain variable domain is from SEQ ID NO: 2. In various embodiments the crystalline anti-huIL-23p19 antibody comprises a heavy chain comprising a γ1 human heavy chain constant region or a γ4 human heavy chain constant region. In another embodiment the binding compound comprises the light chain sequence of SEQ ID NO: 4 and heavy chain sequence selected from the group consisting of SEQ ID NOs: 1-3. In a preferred refinement of the preceding embodiment, the heavy chain sequence is SEQ ID NO: 2.

In various embodiments, the invention relates use of the crystalline formulations of the present invention in the treatment of, or in methods of treatment of, or in the manufacture of medicaments for the treatment of, disorders including but not limited to inflammatory disease, autoimmune disease, proliferative disorders, cancer, and infectious disease (e.g. bacterial, mycobacterial, viral or fungal infection, including chronic infections), such as psoriasis, psoriatic arthritis, rheumatoid arthritis (RA), inflammatory bowel diseases (IBD) such a Crohn's disease (CD) and ulcerative colitis (UC), ankylosing spondylitis (AS), graft-versus-host disease (GVHD), multiple sclerosis (MS), uveitis, systemic lupus erythematosus (SLE) and diabetes (IDDM). The invention also relates to pharmaceutical compositions comprising the crystalline suspension of the present invention for treating these disorders.

In some embodiments, the crystalline suspension of the present invention is delivered intravenously. In other embodiments, the crystalline suspension of the present invention is delivered subcutaneously. In yet other embodiments, the crystals of the present invention are delivered, e.g., by inhalation or insufflation.

In some embodiments, the crystalline suspension or pharmaceutical compositions of the present invention provide prolonged pharmacokinetics of the anti-human IL-23 antibody, such as the anti-human IL-23p19 antibody. In various embodiments, crystalline formulations or pharmaceutical compositions of the present invention are dosed at intervals of 12-, 13-, 16-, 20-, 24-, 26-, 30-, 39-, or 52-weeks, or longer.

In another aspect, the invention relates to methods of preparing the anti-huIL-23 antibody crystals, such as the anti-human IL-23p19 antibody crystals, of the present invention. In one embodiment, the crystalline anti-human IL-23 antibody, such as the anti-human IL-23p19 antibody, of the present invention is made by a batch crystallization method comprising the steps of mixing a solution of the antibody (antibody solution) with a precipitant solution to form a crystallization solution, incubating that crystallization solution for a time sufficient for crystal formation (crystallization), and harvesting the crystals from the solution. In some embodiments, an equal volume of precipitant solution is added to form the crystallization solution.

In some embodiments, the precipitant solution comprises a buffer with a pH between 4 and 8, such as 4.5, 5.5, 7.5, or any other suitable value. In various embodiments, the buffers are sodium citrate, sodium acetate, HEPES, or BisTris.

In some embodiments, the precipitant solution comprises 5-70% 1,2 propanediol, such as 10%, 20%, 30% or any other suitable value. In related embodiments, the crystallization solution comprises 2.5-35% 1,2 propanediol, such as 5%, 10%, 15% or any other suitable value.

In some embodiments, the precipitant solution comprises 5-70% PEG 300, such as 14%, 40%, 70% or any other suitable value. In related embodiments, the crystallization solution comprises 2.5-35% PEG 400, such as 7%, 20%, 35% or any other suitable value. In other embodiments, the precipitant solution comprises 5-70% PEG 400, such as 20%, 25%, 27%, 30% or any other suitable value. In related embodiments, the crystallization solution comprises 2.5-35% PEG 300, such as 10%, 12.5%, 13.5%, 15% or any other suitable value.

In one embodiment, the precipitant solution comprises 1,2 propanediol; HEPES (pH 7.5); and PEG 400, e.g. 30% 1,2 propanediol; 0.1 M HEPES (pH 7.5); and 20% PEG 400. In a related embodiment, the crystallization solution may comprise, e.g., 15% 1,2 propanediol; 0.05 M HEPES (pH 7.5); and 10% PEG 400.

In another embodiment, the precipitant solution comprises PEG 300; sodium acetate (pH 4.5); and NaCl, e.g. 70% PEG 300; 0.1 M sodium acetate (pH 4.5); and 0.2 M NaCl. In a related embodiment, the crystallization solution may comprise, e.g., 35% PEG 300; 0.05 M sodium acetate (pH 4.5); and 0.1 M NaCl.

In some embodiments, the antibody solution (i.e. the solution that is mixed with the precipitation solution to create the crystallization solution) comprises the anti-human IL-23 (e.g. anti-human IL-23p19) antibody, sodium citrate (pH 4-6), 4-10% sucrose, 0.1-0.5% polysorbate 80. In one embodiment, the antibody solution comprises about 100 mg/ml anti-human IL-23 (e.g. anti-human IL-23p19) antibody, about 10 mM sodium citrate (about pH 4.8), about 7% sucrose, and about 0.25% polysorbate 80.

In another embodiment, the precipitant solution comprises PEG 300 or PEG 400 and sodium citrate (pH 4-6), e.g. 57.4% PEG 300 and 0.1 M sodium citrate (pH 5.1). In a related embodiment, the crystallization solution may comprise, e.g., about 28.7% PEG 300; 0.055 M sodium citrate (pH 4.8-5.1). In this embodiment the crystallization solution also comprises about 50 mg/ml antibody, about 3.5% sucrose, and about 0.125% polysorbate 80.

In some embodiments anti-human IL-23 (or anti-human IL-23p19) antibody is present at 5-70 mg/ml in the antibody solution, e.g. about 60 mg/ml. In a related embodiment, anti-human IL-23p19 antibody is present at 2.5-35 mg/ml in the crystallization solution. In other embodiments anti-human IL-23 (or anti-human IL-23p19) antibody is present at about 100 mg/ml in the antibody solution. In a related embodiment, anti-human IL-23p19 antibody is present at about 50 mg/ml in the crystallization solution.

In some embodiments the incubation is performed between 10-40° C., e.g. at room temperature (e.g. 22° C.), for 18 hours, 1 day, 5 days or 10 days, or any other time sufficient to allow crystal formation. In other embodiments, the temperature is ramped-up during the incubating step, e.g. from 4° C. up to 10-40° C. In other embodiments, incubation is performed at about 30° C. for 24 hours, optionally with agitation, such as on a rotating platform or nutator.

In some embodiments, the crystallization solution is seeded with crystals (pre-existing crystals of the antibody to be crystallized) during the incubating step.

In another embodiment, the crystalline anti-huIL-23 antibody crystals, such as the anti-human IL-23p19 antibody crystals, of the present invention are prepared by a bulk dialysis crystallization method comprising the steps of dialyzing a solution of anti-human IL-23 antibody, such as the anti-human IL-23p19 antibody, against a dialysis solution for a time sufficient for crystal formation (crystallization), and harvesting the crystals from the retentate.

In some embodiments, the dialysis solution comprises a buffer with a pH between 4 and 8, such as 4.5, 5.5, 7.5, or any other suitable value.

In some embodiments, the dialysis solution comprises 2.5-35% 1,2 propanediol, such as 5%, 10%, 15% or any other suitable value. In some embodiments, the dialysis solution comprises 2.5-35% PEG 400, such as 10%, 12.5%, 13.5%, 15%, 20%, 35% or any other suitable value. In one embodiment, the dialysis solution comprises 1,2 propanediol; HEPES (pH 7.5); and PEG 400, e.g. 10% 1,2 propanediol; 0.1 M HEPES (pH 7.5); and 20% PEG 400.

In other embodiments, the dialysis solution comprises 2.5-35% PEG 300, such as 7%, 14%, 20%, 35% or any other suitable value. In another embodiment, the dialysis solution comprises PEG 300; sodium citrate (pH 5.5); and NaCl, e.g. 14% PEG 300; 0.1 M sodium citrate (pH 5.5); and 0.2 M NaCl.

In some dialysis-based embodiments the anti-human IL-23 antibody, such as the anti-human IL-23p19 antibody, is present at 5-70 mg/ml in the antibody solution, e.g. about 60 mg/ml.

In some embodiments of the bulk dialysis method, the dialysis is performed between 10-40° C., e.g. at room temperature (e.g. 22° C.), for 18 hours, 1 day, 5 days or 10 days, or any other time sufficient to allow crystal formation. In other embodiments, the temperature is ramped-up during dialysis, e.g. from 4° C. up to 10-40° C.

In some embodiments of the bulk dialysis method, the crystallization solution is agitated during the dialysis. In other embodiments, the antibody solution/retentate is seeded with crystals at some point during the dialysis.

In one aspect, the invention relates to crystalline anti-human IL-23 antibodies, such as anti-human IL-23p19 antibodies, made by the methods of the present invention.

In a further aspect, the invention provides methods of purifying anti-huIL-23 antibodies, such as anti-human IL-23p19 antibodies, comprising crystallizing the antibody, using methods of the present invention, and then re-dissolving the antibody prior to use. In another aspect, the invention provides preparations of anti-huIL-23 antibodies such as anti-human IL-23p19 antibodies, that have been purified by the crystallization methods described herein. In yet a further aspect, the invention provides methods of preparing crystals of anti-huIL-23 antibodies, such as anti-human IL-23p19 antibodies, for use in structure determination, e.g. by X-ray diffraction methods.

BRIEF DESCRIPTION OF THE DRAWINGS

FIGS. 11A and 11B are at 70×and 200×magnification, respectively.

DETAILED DESCRIPTION

Figure 1:
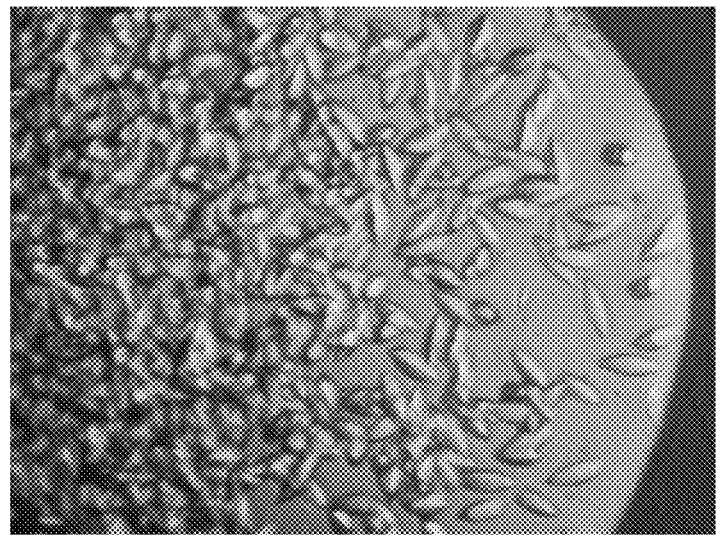
FIG. 1 is a photomicrograph of crystals within an anti-huIL-23p19 mAb crystalline suspension, obtained by vapor diffusion. Anti-huIL-23p19 mAb 13B8-b was crystallized from a solution comprising 30% 1,2 propanediol, 0.1 M HEPES (pH 7.5), and 20% PEG 400. The photomicrograph, at 70×magnification, was taken after 10 days at 18° C. See Example 2.

As used herein, including the appended claims, the singular forms of words such as "a," "an," and "the," include their corresponding plural references unless the context clearly dictates otherwise. Table 5 below provides a listing of sequence identifiers used in this application. All references cited herein are incorporated by reference to the same extent as if each individual publication, patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also include in vitro and ex vivo treatments, e.g., of a cell, by a reagent, diagnostic, binding composition, or by another cell.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) J. Mol. Biol. 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |

TABLE 1-continued

Exemplary Conservative Amino Acid Substitutions

| Original residue | Conservative substitution |
|---|---|
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus the terms encompass, but are not limited to, circumstances in which a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an IL-23p19 specific antibody that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

To examine the extent of inhibition of IL-23 activity, for example, samples or assays comprising a given, e.g., protein, gene, cell, or organism, are treated with a potential inhibiting agent, such as an anti-huIL-23p19 mAb, and are compared to control samples without the agent. Control samples, i.e., not treated with agent, are assigned a relative activity value of 100% Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case IL-23p19) if it binds to polypeptides comprising the sequence of IL-23p19 but does not bind to proteins lacking the sequence of IL-23p19. For example, an antibody that specifically binds to a polypeptide comprising IL-23p19 may bind to a FLAG®-tagged form of IL-23p19 but will not bind to other FLAG®-tagged proteins.

"Interleukin-23" (or "IL-23") means a protein consisting of two polypeptide subunits, p19 and p40. The sequence of the human p19 subunit (also known as IL-23p19, IL-23A) is provided at NCBI Protein Sequence Database Accession Number NP_057668. The sequence of the human p40 subunit (also known as IL-12p40, IL-12B) is provided at NCBI Protein Sequence Database Accession Number NP_002178.

As used herein, "anti-human IL-23p19" and "anti-huIL-23p19" refer to antibodies that specifically bind to the p19 subunit of human interleukin (IL-23). Unless otherwise indicated, or clear from the context, "IL-23" and "IL-23p19" refer to their respective human forms. Unless otherwise indicated, or clear from the context, antibodies referred to herein are monoclonal antibodies.

As used herein, an "antibody solution" may be used to refer to a solution of an anti-huIL-23p19 antibody that is used to generate the crystalline antibody of the present invention. "Precipitant solution" refers to a second solution that is mixed with the antibody solution, typically at a 1:1 volume ration (i.e. equal volumes of the two solutions are mixed) to create a "crystallization solution" from which antibodies grow. The concentrations of the antibody and precipitant solutions are provided herein for a 1:1 mixture, for convenience, but one of skill in the art would recognize that the volume ratio used to make the mixture can be changed, and thus so can the concentrations of the solutions making up the mixture. Such modifications are within the scope of the invention if they generate the same crystallization conditions (i.e. the same crystallization solution) as the mixtures described herein.

As used herein, and with regard to crystallization methods based on dialysis, "dialysis solution" refers to the solution against which a solution of anti-huIL-23p19 antibody (the "antibody solution") is dialyzed to drive formation of the crystalline antibody of the present invention. "Retentate" refers to the antibody solution after dialysis, which may include crystals of the antibody, which are harvested. The antibody solution/retentate are on one side of the dialysis membrane, and the dialysis solution is on the opposite side.

A "precipitant" is a compound that decreases the solubility of a polypeptide, such as an antibody, in a concentrated solution. In batch crystallization methods the precipitant is included in the "precipitant solution," and in bulk dialysis methods the precipitant is included in the "dialysis solution." Precipitants induce crystallization by forming an energetically unfavorable precipitant-depleted layer around the polypeptide molecules. To minimize the relative amount of this depletion layer, the polypeptides form associations and, ultimately, crystals. This process is explained in Weber (1991) *Advances in Protein Chemistry* 41:1, which is incorporated by reference. Various precipitants are known in the art and include: ammonium sulfate, ethanol, isopropanol, 1,2 propanediol, 3-ethyl-2,4 pentanediol; and many of the polyglycols, such as polyethylene glycol (e.g. PEG 300 and PEG 400). In addition to precipitants, other materials are sometimes added to the polypeptide precipitant solution. These include buffers, such as Tris or HEPES, to adjust the pH of the solution (and hence surface charge on the peptide) and salts, such as sodium chloride, lithium chloride and sodium citrate, to reduce the solubility of the polypeptide.

When used with reference to a crystalline antibody suspension of the present invention, "concentration" refers to the amount of antibody (in this case anti-huIL-23p19 antibody) present in a given macroscopic unit volume of solution. The term concentration is used in its customary sense despite the inherent heterogeneity of the suspension, as compared to a traditional solution. The concentration of antibody in a crystalline suspension is equal to the concentration of an equivalent sample in which the antibody was not in crystalline form.

II. General

The present invention provides crystalline forms of anti-huIL-23p19 antibodies, suspensions of these crystals, and pharmaceutical formulations of these suspensions. Highly purified anti-human interleukin-23p19 monoclonal antibody hu13B8-b was used in high throughput (HT) vapor diffusion sparse matrix experiments. Crystalline suspensions were obtained at room temperature using low molecular weight PEGs (300 and 400) and 1,2 propanediol, or under other conditions as disclosed herein. Conditions were established to prepare crystalline suspensions by bulk crystallization methods (batch and dialysis) in high yield. The resulting crystalline suspensions have a particle size of 5-200 microns. Antibody obtained by re-dissolving the crystals have been characterized by ELISA, SDS PAGE, and dynamic light scattering. The properties of the re-dissolved crystalline antibody are similar to those of the original antibody starting sample in all biophysical characterization studies.

Crystalline anti-huIL-23p19 antibodies of the present invention have several advantageous properties for use in therapy. The crystalline suspensions of anti-huIL-23p19 antibodies of the present invention can also be prepared at higher concentrations that solution formulations. This high concentration can enable more efficient administration to subject, e.g. by subcutaneous injection. For example, solution formulations at 100 mg/ml cannot be used to deliver more than 100 mg to a subject with a single subcutaneous injection due to limitations of how much volume can be practically delivered at a single injection site. This limits dosing to approximately 1.5 mg/kg, unless the subject is willing to accept (and in some cases administer) multiple injections at multiple sites. The crystalline suspensions of the present invention, in contrast, can be used to prepare pharmaceutical formulations up to 200 mg/ml or more, enabling higher dosing with lower injection volume, and thus less discomfort. The crystalline suspensions of the present also have significantly lower viscosity than high concentration solution formulations, facilitating administration by syringe, and/or enabling use of a smaller needle for injection. Crystalline suspensions of the present invention may be delivered by subcutaneous injection using small bore needles, such as 28 G insulin syringes. The reduced volume, decreased viscosity and use of a smaller needle are all likely to decrease patient discomfort accompanying subcutaneous administration of anti-huIL-23p19 antibodies, which is of particular concern when a drug of intended for self-administration (e.g. by prefilled syringe or autoinjector).

The crystalline suspensions of anti-huIL-23p19 antibodies of the present invention also exhibit superior properties with regard to the pharmacokinetics of drug delivery. Compared with the corresponding solution formulations, the crystalline suspensions of the present invention exhibit delayed bioavailability. This time-released delivery of the drug (anti-huIL-23p19 antibody) into the circulation in the subject can advantageously increase the time over which the drug is present at an effective dose for a given administration. This can reduce the initial spike in drug concentration that would otherwise occur soon after administration (e.g. subcutaneous delivery of a solution formulation), and may enable less frequent dosing.

Crystalline anti-huIL-23p19 antibodies of the present invention also have other advantageous properties. Suspensions of the crystalline anti-huIL-23p19 antibodies will likely have improved stability compared with corresponding solution formulations, i.e. the crystalline suspensions will retain anti-IL-23 biological activity for a longer time. Suspensions of the crystalline anti-huIL-23p19 antibodies of the present invention can even be stored at room temperature, whereas typical solution formulations would have to be stored at 4° C. The longer shelf-life, and the ability to store the suspensions of the present invention a room temperature, offer significant advantages in handling of drug product and supply chain management.

Re-dissolved crystalline anti-huIL-23p19 antibodies of the present invention are characterized at Example 6. These results demonstrate the re-dissolved crystalline antibodies of the present invention retain the binding affinity and biological activity (IL-23 neutralization) of the starting material, and thus that they are suitable for all purposes for which the original antibody was suited, e.g. therapeutic treatment of human subjects. Specifically, the re-dissolved crystalline anti-huIL-23p19 antibodies of the present invention are substantially similar as assessed by SDS-PAGE, and dynamic light scattering shows that the re-dissolved antibody remains monodisperse with approximately the same experimentally observed molecular weight. See Table 3, Example 6. The re-dissolved crystalline anti-huIL-23p19 antibodies of the present invention also exhibit substantially similar EC50 values when compared with starting material in an ELISA. See Table 4, Example 6.

Accordingly, crystalline anti-huIL-23p19 antibodies that retain the properties of the pre-crystallization starting material within acceptable tolerances are encompassed in embodiments of the present invention. Acceptable tolerances for the various functional parameters may vary based on the intended use, but with regard to binding affinity or biological activity, may include retention of 100%, 90%, 75%, 50% or 25% of the original (non-crystallized) affinity or activity. For example, acceptable $K_D$ or EC50/IC50 values may include 1, 2, 3, 4 or 5× the original (non-crystallized) $K_D$ or EC50/IC50 values, since these increased numerical values correspond to decreased binding affinity and biological activity. Methods for determining binding affinity and biological (neutralizing) activity are found at Examples 9-12.

The anti-huIL-23p19 antibody crystals themselves are characterized in Example 7. X-ray diffraction demonstrates that the anti-huIL-23p19 antibody crystals are characterized by unit cell dimensions of a=192 Å, b=192 Å, c=106 Å, $\alpha$=90°, $\beta$=90°, $\gamma$=90° and are in space group I4. Crystals of anti-huIL-23p19 antibodies exhibiting substantially similar properties are also encompassed in embodiments of the present invention.

The invention further provides various methods for making the crystalline anti-huIL-23p19 antibody of the present invention, as described in greater detail in Examples 2-4. Example 2 provides methods based on vapor diffusion, which are best suited for screening to determine preferred crystallization conditions, rather than for large scale crystal production. Such methods may also be suitable for generation of large crystals for use in X-ray diffraction studies, e.g. to determine the three dimensional structure of the anti-huIL-23p19 antibody.

With regard to commercial scale production of crystalline anti-huIL-23p19, e.g. for therapeutic use, Examples 3 and 4 provide crystallization protocols more suited to large-scale production, such as batch crystallization and bulk dialysis crystallization. Two independent sets of solution conditions are provided for each example, one at pH 7.5 and the other at pH 4.5. The methods disclosed in Examples 3 and 4 amenable to being scaled-up for commercial scale production. Example 5 provides a method of harvesting crystals of the present invention using centrifugation, but filtration methods know in the art, such as hollow fiber tangential flow filtration, may also be used to harvest crystals, e.g., at commercial scale. Although the specific disclosed embodiments employ a 1:1 mixture of an antibody solution with a precipitant solution, any modification of the method that ends up with approximately the same concentrations of solution components in the final crystallization solution (from which crystals arise) would be equivalent. Specifically, the concentrations of the components in the precipitant solution may be proportionally increased or decreased if the precipitant solution comprises less than or more than 50% of the final volume of the crystallization solution, respectively.

The crystallization methods of the present invention also provide a method of purifying anti-huIL-23p19 antibodies, even if such crystals are re-dissolved prior to use. In one embodiment, an anti-huIL-23p19 antibody is produced and at least partially purified by methods described elsewhere herein (Section VII) and known in the art. The antibody is then crystallized, e.g. by batch crystallization as described in Example 3, or by bulk dialysis as described in Example 4. The crystalline antibody was then recovered and washed, e.g. as described in Example 5 (or by filtration), and re-dissolved essentially as described in the first paragraph of Example 6 except that the resuspension buffer need not be 10 mM sodium citrate (pH 5.5), but can instead be any suitable buffer for the intended use of the purified antibody. For therapeutic uses, suitable pharmaceutically acceptable buffers and excipients would be used.

III. Protein Crystallization

Various methods of crystallization are known. Giege et al. (1994) *Acta Crystallogr.* D50:339; McPherson (1990) *Eur. J. Biochem.* 189:1. Such techniques include hanging drop vapor diffusion (McPherson (1976) *J. Biol. Chem.* 251: 6300), sitting drop vapor diffusion, microbatch and dialysis. Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water vaporizes from the drop and transfers to the reservoir, the precipitant concentration increases to a level optimal for crystallization. Since the system is in equilibrium, these optimum conditions are maintained until the crystallization is complete. The hanging drop method differs from the sitting drop method in the vertical orientation of the protein solution drop within the system. In the microbatch method, polypeptide is mixed with precipitants to achieve supersaturation, and the vessel is sealed and set aside until crystals appear. In the dialysis method, polypeptide is retained on one side of a dialysis membrane which is placed into contact with a solution containing precipitant. Equilibration across the membrane increases the precipitant concentration thereby causing the polypeptide to reach supersaturation levels. For the methods of the present invention, it is desirable to use an anti-huIL-23p19 antibody at an initial protein concentration of about 5-100 mg/ml, such as 60 mg/ml or 100 mg/ml.

Uniform crystalline suspensions of therapeutic proteins present opportunities for novel drug delivery systems. Crystalline insulin suspensions have been used as sustained release preparations for over fifty years (Brange et al. (1999) *Adv. Drug Deliv. Rev.* 35:307). Crystalline suspensions have also been proposed for the delivery of interferon (U.S. Pat.

No. 5,972,331) and monoclonal antibodies (Yang et al. (2003) *Proc. Nat'l Acad. Sci. (USA)* 100:6934). Crystalline forms also enable non-injectable delivery systems such as pulmonary delivery for local or systemic delivery of protein therapeutics (U.S. Pat. No. 5,972,331).

Henry Bence Jones was the first to describe naturally occurring crystals of immunoglobulin light chains, the so-called "Bence-Jones protein," isolated the urine of a myeloma patient. Jones (1848) *Phil. Trans. Royal Soc. (London)* 55-62. Full-length, intact antibodies, however, are difficult to crystallize, likely due to the flexibility of their multiple (four) polypeptide chains. Although, there have been numerous reports of crystallization of intact antibodies over the last 30 years, only four structures have been deposited in the Research Collaboratory for Structural Bioinformatics Protein Databank (RCSB-PDB). In contrast, there have been over 800 structures deposited for antibody fragments, such as Fab fragments (either apo or complexed).

Some full-length therapeutic antibodies have been crystallized. Determination of the crystal structure for an anti-human IL-13 antibody is described at Int'l Pat. App. Pub. WO 2005/121177 (issued as U.S. Pat. No. 7,615,213) to Wyeth, and methods for the preparation of crystalline anti-human TNF-α crystals are described at Int'l Pat. App. Pub. WO 2008/057240 (issued as U.S. Pat. No. 8,034,906) to Abbott Biotechnology. Ltd. Methods for the preparation of crystalline anti-human IL-12 antibodies are described at Int'l Pat. App. Pub. WO 2008/121301 (issued as U.S. Pat. No. 8,168,760) to Abbott Laboratories.

Protein crystals, including antibodies, are also being developed as therapeutic compositions. Altus Pharmaceuticals, now a part of Althea Technologies, Inc., has put three crystalline protein formulations into human clinical trials: ALTU-238 (long-acting injectable formulation of somatropin); ALTU-237 (oral oxalate-degrading enzyme); and ALTU-236 (oral phenylalanine degrading enzyme). Researchers from Altus also crystallized three commercially available monoclonal antibodies (rituximab, trastuzumab and infliximab) by vapor diffusion methods or batch crystallization. Yang et al. (2003) *Proc. Nat'l Acad. Sci. (USA)* 100:6934; Int'l Pat. App. Pub. WO 02/072636, issued as U.S. Pat. No. 7,833,525). The resulting high concentration, low viscosity crystals were obtained in high yield, and showed excellent physical and chemical stability, as well as retention of biological activity in vitro. Subcutaneous injection of trastuzumab and infliximab crystalline suspensions resulted in an extended serum pharmacokinetic profile and high bioavailability compared with the soluble forms of the antibodies delivered intravenously. The crystalline formulation of trastuzumab was also effective in a preclinical model of human breast cancer. Spherical protein particles of therapeutic antibodies are disclosed at U.S. Pat. No. 7,998,477.

Crystallization by methods of the present invention also provides an improved method of purification of anti-huIL-23p19 antibodies. Although macro-scale crystallization is frequently used in purification of small organic molecules, there are few examples of the use of crystallization in the preparation of proteins. An exception is the use of a crystallization step in the manufacture of interferon alpha-2b (IFN-$\alpha_{2b}$), where a temperature induction method is used in the purification process on a multigram scale. The resulting crystalline suspension is harvested by centrifugation, washed and solubilized in a cold normal saline phosphate buffer. The crystallization and harvesting process removes small molecule, interferon-related and non-interferon impurities that may remain in the mother liquor or wash. Crystallization also confirms the purity of the therapeutic protein.

IV. IL-23 Biology

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12β1, which is shared by the IL-12 receptor. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23 (see, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948). Additional information relating to IL-23 (IL23A) may be found at NCBI's Gene Database under GeneID 51561, and at the Online Mendelian Inheritance in Man database under MIM 605580, each of which is hereby incorporated by reference.

Recent studies, through the use of p40 KO mice, have shown that blockade of both IL-23 and IL-12 is an effective treatment for various inflammatory and autoimmune disorders. IL-23 is known to play a central role in psoriasis, and the IL-23/IL-12 antagonist antibody ustekinumab (anti-IL-12/23p40 mAb) has been approved in the U.S. and Europe for the treatment of psoriasis. However, the blockade of IL-12 through p40 appears to have various systemic consequences such as increased susceptibility to opportunistic microbial infections. Bowman et al. (2006) *Curr. Opin. Infect. Dis.* 19:245.

V. Anti-Human IL-23 Anitbody-13B8-b

The present application discloses data relating to crystallization of the anti-human IL-23p19 antibody clone 13B8-b, as described and claimed in commonly assigned WO 2008/103432, the disclosure of which is hereby incorporated by reference in its entirety. WO 2008/103432 discloses a humanized anti-huIL-23p19 antibody, designated 13B8-a, and two variants differing only at residues in CDRH2, designated 13B8-b and 13B8-c. The CDRH2 sequences are provided at Table 2. The humanized light chain 13B8 sequence (with kappa constant region) is provided at SEQ ID NO: 4, and the light chain variable domain comprises residues 1-108 of that sequence. Three versions of the humanized heavy chain 13B8 sequence (with γ1 constant regions) are provided at SEQ ID NOs: 1-3, and the heavy chain variable domain comprises residues 1-116 of those sequences.

TABLE 2

Antibody 13B8 CDRH2 Variants

| Antibody | CDRH2 Sequence | SEQ ID NO: |
|---|---|---|
| 13B8-a | QIFPASGSADYNEMFEG | 6 |
| 13B8-b | QIFPASGSADYNEKFEG | 7 |
| 13B8-c | QIFPASGSADYAQKLQG | 8 |

A hybridoma expressing the parental (mouse) antibody 13B8 was deposited pursuant to the Budapest Treaty with American Type Culture Collection (ATCC-Manassas, Va., USA) on Aug. 17, 2006 under Accession Number PTA-7803. All restrictions on the accessibility of this deposit will be irrevocably removed upon the granting of a U.S. patent based on the present application.

VI. Additional Anti-Human IL-23 Antibodies

The heterodimeric nature of IL-23 suggests that antagonist antibodies may bind exclusively to the p40 subunit, exclusively to the p19 subunit, or exclusively to the IL-23 complex (p40 and p19). IL-23 antagonist antibodies have been reported in all three of these categories. Although the results presented herein were obtained exclusively with humanized anti-human IL-23p19 antibody clone 13B8-b, it is possible that the methods used herein could be used to crystallize these other anti-IL-23 antagonist antibodies as well. In some such prophetic embodiments, the IL-23 antagonist antibody binds to the p40 subunit of IL-23 and IL-12. Examples include ustekinumab (CNTO 1275) and briakinumab (ABT-874, J-695). Ustekinumab is marketed by Centocor for the treatment of psoriasis, and is described at U.S. Pat. Nos. 6,902,734 and 7,166,285 (to Centocor, Inc.), the disclosures of which are hereby incorporated by reference in their entireties. Specifically, the sequences of SEQ ID NOs: 7 (heavy chain variable domain) and 8 (light chain variable domain), of U.S. Pat. No. 6,902,734 are hereby incorporated by reference. SEQ ID NOs: 4-5-6 and 1-2-3 of U.S. Pat. No. 6,902,734 are also incorporated by reference. Briakinumab was developed by Abbott, and is described at U.S. Pat. Nos. 6,914,128 and 7,504,485, the disclosures of which are hereby incorporated by reference in their entireties. Sequences for ustekinumab are also provided at SEQ ID NOs: 16-25 of the sequence listing of the present application. Specifically, the sequences of SEQ ID NOs: 31 (heavy chain variable domain), 32 (light chain variable domain) SEQ ID NOs; 30-28-26 (light chain CDRs 1-2-3, respectively) and 29-27-25 (heavy chain CDRs 1-2-3, respectively) of U.S. Pat. No. 6,914,128 are hereby incorporated by reference. Sequences for briakinumab are also provided at SEQ ID NOs: 26-35 of the sequence listing of the present application. Examples also include an antibody that binds specifically to IL-23p40 but not IL-12p40 as disclosed in U.S. Pat. No. 7,247,711 (to Centocor).

In other prophetic embodiments, the IL-23 antagonist antibody binds to the p19 subunit of IL-23. Examples include Eli Lilly's LY2525623 and Centocor's CNTO 1959, both of which have entered human clinical trials. Specifically, the sequences of SEQ ID NOs: 48 and 52 (heavy chain variable domains), 57 (light chain variable domain), 28-37-40 (light chain CDRs 1-2-3, respectively) and 3-8-19 (light chain CDRs 1-2-3, respectively) of EP 1937721 B1 (to Eli Lilly and Company) are hereby incorporated by reference. In addition, the sequences of SEQ ID NOs: 106 (heavy chain variable domain), 116 (light chain variable domain), 50-56-73 (light chain CDRs 1-2-3, respectively) and 5-20-44 (light chain CDRs 1-2-3, respectively) of U.S. Pat. No. 7,935,344 (to Centocor) are also hereby incorporated by reference. Further examples include monoclonal antibody FM303 (Femta Pharmaceuticals), and the antibodies disclosed at WO 2008/103432, US 2007/0048315 and WO 2008/103473 (to Schering Corp.); U.S. Pat. Nos. 7,491,391, 7,935,344 and EP 1971366 A2 (to Centocor Ortho Biotech, Inc.); U.S. Pat. No. 7,872,102 (to Eli Lilly and Co.); WO 2007/147019, WO 2008/134659 and WO 2009/082624 (to Zymogenetics); US 2009/0311253 (to Abbott Bioresearch); and US 2009/0123479 and WO 2010/115786 (to Glaxo SmithKline), the disclosures of which are hereby incorporated by reference in their entireties.

In yet further prophetic embodiments, the IL-23 antagonist antibody binds to the IL-23 complex rather than to the individual subunits. Examples include an antibody that makes contacts with both the p19 and p40 subunits of IL-23 (WO 2011/056600 to Amgen, Inc.) and an antibody that binds to IL-23 but not significantly to either of its individual subunits (WO 2012/009760 to Cephalon Australia Pty., Ltd).

Further exemplary non-specific IL-23 antagonist antibodies that bind to the p40 subunit of IL-23 and IL-12 are disclosed at Clarke et al. (2010) mAbs 2:1-11 (Cephalon Australia, Pty., Ltd.). FM202 (Femta Pharmaceuticals) is also a monoclonal antibody that binds to the p40 subunit of both IL-12 and IL-23, as are the antibodies disclosed at WO 2010/017598 (Arana Therapeutics, Ltd.).

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-huIL-23p19 antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate (pH 5.5).

In another embodiment, the antibodies of the present invention are produced in yeast according to the methods described in WO 2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-IL-23p19 antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for IL-23) to those of the original antibodies. See. e.g., WO 2005/040395.

VIII. Pharmaceutical Compositions

To prepare pharmaceutical or sterile compositions, the crystalline anti-human IL-23p19 antibodies of the present invention are mixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Crystalline antibody compositions of the present invention can be provided by continuous infusion, or by doses at intervals of, e.g., one day, 1-7 times per week, one week, two weeks, monthly, bimonthly, quarterly, biannually, annually, etc. Doses may be provided intravenously, subcutaneously, intramuscularly, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

Crystalline formulations of anti-huIL-23p19 antibodies of the present invention may enable administration at levels that are not otherwise practical using standard solution formulations, such as administration at 100, 15, 200, 250 mg/ml or higher concentrations. Such high concentration delivery enables delivery of high doses by subcutaneous injection, in which there exists a practical limit of approximately 1 ml for the volume that can be delivered in any given injection. Crystalline formulations of anti-huIL-23p19 antibodies of the present invention may also enable modes of administration that are not otherwise practical, such as oral, pulmonary or needle-free delivery.

IX. Uses

The present invention provides methods for using engineered anti-huIL-23 antibodies and fragments thereof for the treatment of inflammatory disorders and conditions, e.g., of the central nervous system, peripheral nervous system, and gastrointestinal tract, as well as autoimmune and proliferative disorders.

Methods are provided for the treatment of, e.g., multiple sclerosis (MS), including relapsing-remitting MS and primary progressive MS, Alzheimer's disease, amyotrophic lateral sclerosis (a.k.a. ALS; Lou Gehrig's disease), ischemic brain injury, prion diseases, and HIV-associated dementia. Also provided are methods for treating neuropathic pain, posttraumatic neuropathies, Guillain-Barre syndrome (GBS), peripheral polyneuropathy, and nerve regeneration.

Provided are methods for treating or ameliorating one or more of the following features, symptoms, aspects, manifestations, or signs of multiple sclerosis, or other inflammatory disorder or condition of the nervous system: brain lesions, myelin lesions, demyelination, demyelinated plaques, visual disturbance, loss of balance or coordination, spasticity, sensory disturbances, incontinence, pain, weakness, fatigue, paralysis, cognitive impairment, bradyphrenia, diplopia, optic neuritis, paresthesia, gait ataxia, fatigue, Uhtoff's symptom, neuralgia, aphasia, apraxia, seizures, visual-field loss, dementia, extrapyramidal phenomena, depression, sense of well-being, or other emotional symptoms, chronic progressive myelopathy, and a symptom detected by magnetic resonance imaging (MRI), including gadolinium-enhancing lesions, evoked potential recordings, or examination of cerebrospinal fluid. See, e.g., Kenealy et al. (2003) *J. Neuroimmunol.* 143:7-12; Noseworthy et al. (2000) *New Engl. J. Med.* 343:938-952; Miller et al. (2003) *New Engl. J. Med.* 348:15-23; Chang et al. (2002) *New Engl. J. Med.* 346:165-173; Bruck and Stadelmann (2003) *Neurol. Sci.* 24 Suppl. 5:S265-S267.

Moreover, the present invention provides methods for treating inflammatory bowel disorders, e.g., Crohn's disease, ulcerative colitis, celiac disease, and irritable bowel syndrome. Provided are methods for treating or ameliorating one or more of the following symptoms, aspects, manifestations, or signs of an inflammatory bowel disorder: malabsorption of food, altered bowel motility, infection, fever, abdominal pain, diarrhea, rectal bleeding, weight loss, signs of malnutrition, perianal disease, abdominal mass, and growth failure, as well as intestinal complications such as stricture, fistulas, toxic megacolon, perforation, and cancer, and including endoscopic findings, such as, friability, aphthous and linear ulcers, cobblestone appearance, pseudopolyps, and rectal involvement and, in addition, anti-yeast antibodies. See, e.g., Podolsky, supra; Hanauer, supra; Horwitz and Fisher, supra.

Also contemplated are treatment of inflammatory disorders such as psoriasis, atopic dermatitis, arthritis, including rheumatoid arthritis, osteoarthritis, and psoriatic arthritis, ankylosing spondylitis, graft-versus-host disease, autoimmune disorders, such as systemic lupus erythematosus and type I diabetes, and proliferative disorders such as cancer. See, e.g., PCT patent application publications WO 04/081190; WO 04/071517; WO 00/53631; and WO 01/18051. Also contemplated is treatment of chronic infections, such as chronic fungal infections, e.g. infections with *Candida* spp. and *Aspergillus* spp. See commonly assigned Int'l Pat. App. Pub. WO 2008/153610.

The IL-23p19 binding compounds of the present invention can also be used in combination with one or more antagonists of other cytokines (e.g. antibodies), including but not limited to, IL-17A, IL-17F, IL-1β, IL-6 and TGF-β. See, e.g., Veldhoen (2006) *Immunity* 24:179-189; Dong (2006) *Nat. Rev. Immunol.* 6(4):329-333. In various embodiments, an IL-23p19 binding compound of the invention is administered before, concurrently with, or after administration of the another antagonist or antagonists, such as an anti-IL-17A antibody. In one embodiment, an IL-17A binding compound is used in treatment of the acute early phase of an adverse immune response (e.g. MS, Crohn's Disease) alone or in combination with an IL-23 antagonist antibody of the present invention. In the latter case, the IL-17A binding compound may be gradually decreased and treatment with the antagonist of IL-23 alone is continued to maintain suppression of the adverse response. Alternatively, antagonists to IL-1β, IL-6 and/or TGF-β may be administered concurrently, before or after an IL-23p19 binding compound of the present invention. See Cua and Kastelein (2006) *Nat. Immunol.* 7:557-559; commonly assigned Int'l Pat. App. Pub. WO 2008/106131; Tato and O'Shea (2006) *Nature* 441:166-168; Iwakura and Ishigame (2006) *J. Clin. Invest.* 116:1218-1222.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning*, 3rd ed., Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science*, Vol. 2, John Wiley and Sons, Inc., New York; Ausbel et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protocols in Immunology*, Vol. 4, John Wiley, Inc., New York.

Example 2

Vapor Diffusion Crystallization of Anti-huIL-23p19 mAb 13B8-b

Figure 2:
FIG. 2 is a photomicrograph of crystals within an anti-huIL-23p19 mAb crystalline suspension, obtained by vapor diffusion. Anti-huIL-23p19 mAb 13B8-b was crystallized from a solution comprising 0.1 M sodium acetate (pH 4.5), 0.2 M NaCl, and 40% PEG 300. The photomicrograph, at 70×magnification, was taken after 10 days at 18° C. See Example 2.

Conditions for preparing crystals of anti-huIL-23p19 mAb 13B8-b were determined as follows. A solution of anti-huIL-23p19 mAb 13B8-b was prepared at 61.9 mg/ml in 10 mM sodium citrate (pH 5.5). The solution was screened in hanging drop vapor diffusion experiments using commercially available screens from Emerald BioStructures (Bainbridge Island, Wash., USA), Qiagen Technologies (Gaithersburg, Md., USA) and Jena Bioscience (Jena, Del.) in crystallization plates from Neuro Probe, Inc. (Gaithersburg, Md., USA). Antibody solution (0.5 µl) was mixed with complimentary reservoir solution (0.5 µl) and suspended over 80 µl of complimentary reservoir solution. Experiments were performed at both 4° C. and 18° C. and monitored microscopically over time. Crystals were observed in experiments at 18° C. after 10 days in the Qiagen screening system using a first complimentary reservoir solution comprising 30% 1,2 propanediol; 0.1 M HEPES (pH 7.5); and 20% PEG 400, and also using a second complimentary reservoir solution comprising 0.1 M sodium acetate (pH 4.5); 40% PEG 300; and 0.2 M NaCl. Photomicrographs of the resulting crystals are provided at FIGS. 1 and 2, respectively.

Figure 3:
FIG. 3 is a photomicrograph of crystals within an anti-huIL-23p19 mAb crystalline suspension, obtained by vapor diffusion. Anti-huIL-23p19 mAb 13B8-b was crystallized from a solution comprising 30% 1,2 propanediol, 0.1 M HEPES (pH 7.5), and 20% PEG 400. The photomicrograph, at 70×magnification, was taken after 10 days at 4° C., and then two days at 22° C. See Example 2.
Figure 4:
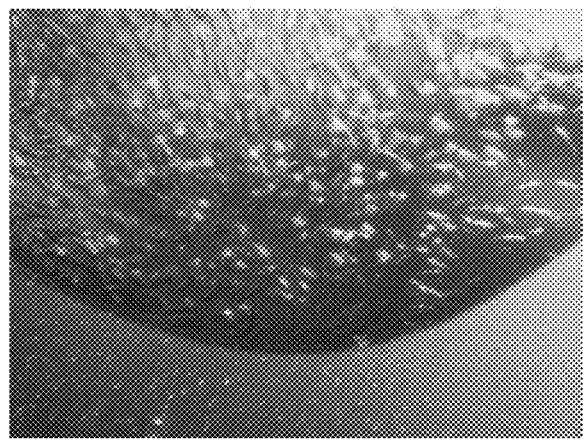
FIG. 4 is a photomicrograph of crystals within an anti-huIL-23p19 mAb crystalline suspension, obtained by vapor diffusion. Anti-huIL-23p19 mAb 13B8-b was crystallized from a solution comprising 0.1 M sodium acetate (pH 4.5), 0.2 M NaCl, and 40% PEG 300. The photomicrograph, at 70×magnification, was taken after 10 days at 4° C., and then two days at 22° C. See Example 2.

Two analogous experiments at 4° C. showed no evidence of crystals after 10 days, but both these experiments produced crystals within two days after the temperature was shifted to 22° C. (room temperature). Photomicrographs of the crystals observed in the 4° C. experiments are provided at FIGS. 3 and 4.

Additional experiments failed to generate any crystals. Crystals were not observed under any conditions in Emerald BioStructures or Jena Bioscience systems. Crystals were also not observed, at either 4° C. or 18° C., under four sets conditions: PP(PEG/salt); HPPEG (PEG/salt); J1 (PEG/salt); J2 (salt).

Example 3

Batch Crystallization of Anti-huIL-23p19 mAb 13B8-b

Figure 5:
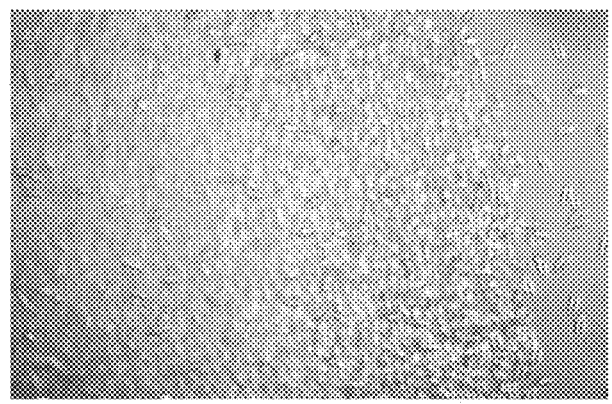
FIG. 5 is a photomicrograph of crystals within an anti-huIL-23p19 mAb crystalline suspension, obtained by batch crystallization at pH 7.5. Anti-huIL-23p19 mAb 13B8-b was crystallized after mixture with a solution comprising 30% 1,2 propanediol, 0.1 M HEPES (pH 7.5), and 20% PEG 400, as discussed at Example 3. The photomicrograph, at 70×magnification, was taken after 18 hours at 22° C. Particle sizes range from about 3-5 microns.

In light of the results obtained in Example 2, batch crystallization of anti-huIL-23p19 mAb 13B8-b at pH 7.5 was performed as follows. A solution of anti-huIL-23p19 mAb 13B8-b was prepared at 60 mg/ml in 10 mM sodium citrate (pH 5.5). 500 µl of this solution was mixed with an equal volume of 30% 1,2 propanediol; 0.1 M HEPES (pH 7.5); and 20% PEG 400 at 4° C. The mixture was incubated for 18 hours at room temperature (22° C.). A photomicrograph of the resulting crystals is provided at FIG. 5. The crystalline suspension was recovered as described in Example 5 at 85% yield.

Figure 6:
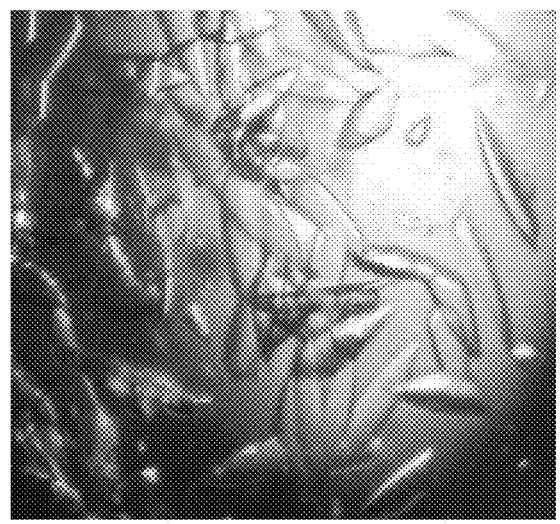
FIG. 6 is a photomicrograph of crystals within an anti-huIL-23p19 mAb crystalline suspension, obtained by batch crystallization at pH 4.5, as discussed at Example 3. Anti-huIL-23p19 mAb 13B8-b was crystallized after mixture with a solution comprising 58% PEG 300, 0.1 M sodium acetate (pH 4.5), and 0.2 M NaCl. The photomicrograph, at 400×magnification, was taken after 18 hours at 22° C. Particle sizes range from about 30-80 microns.

Batch crystallization of anti-huIL-23p19 mAb 13B8-b was also performed at pH 4.5, as follows. A solution of anti-huIL-23p19 mAb 13B8-b was prepared at 60 mg/ml in 10 mM sodium citrate (pH 5.5). 500 μl of this solution was mixed with an equal volume of 70% PEG 300; 0.1 M sodium acetate (pH 4.5); and 0.2 M NaCl at 4° C. The mixture was incubated for 18 hours at room temperature (22° C.). A photomicrograph of the resulting crystals is provided at FIG. 6. The crystalline suspension was recovered as described in Example 5 at 70% yield.

Figure 9:
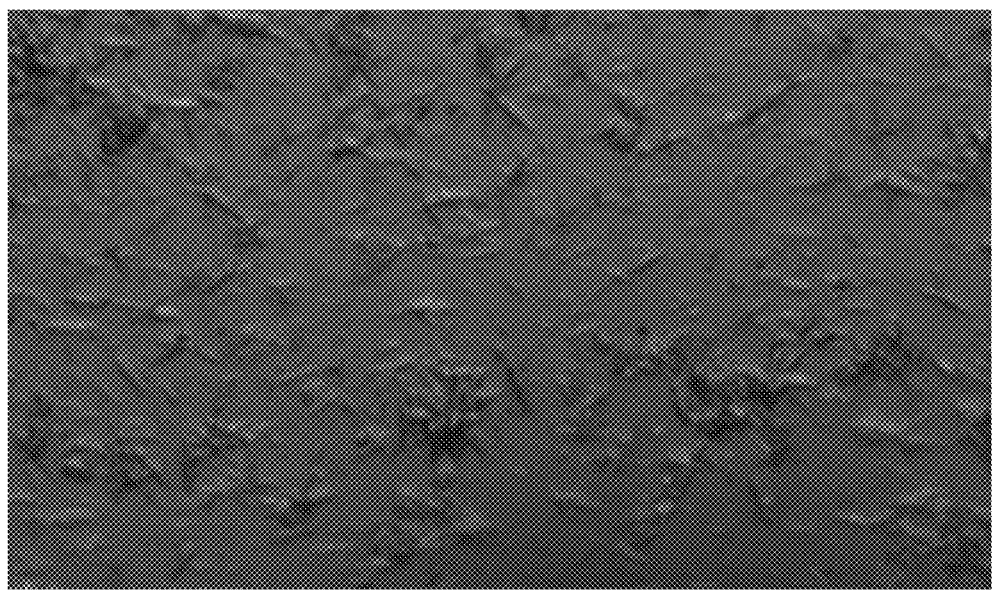
FIG. 9 is a photomicrograph (at 170×magnification) of crystals within an anti-huIL-23p19 mAb crystalline suspension, obtained by batch crystallization as discussed at Example 4 (last paragraph).

Alternatively, batch crystallization of anti-huIL-23p19 mAb 13B8-b was performed as follows. A solution of anti-huIL-23p19 mAb 13B8-b was prepared at 100 mg/ml in 10 mM sodium citrate (pH 4.8), 7% sucrose, 0.25% polysorbate 80. 500 μl of this solution was mixed with an equal volume of 100 mM sodium citrate (pH 5.1), 57.4% PEG 300 at 22° C. The mixture was placed on a ClayAdams nutator mixer (BD Diagnostics Part No. 421105) (VWR International LLC, Radnor, Penna., USA) and incubated 24 hours at 30° C. A photomicrograph of the resulting crystals is provided at FIG. 9. The crystalline suspension was recovered as described in Example 5 at 90% yield.

Example 4

Bulk Dialysis Crystallization of Anti-huIL-23p19 mAb 13B8-b

Figure 7:
FIG. 7 is a photomicrograph of crystals within an anti-huIL-23p19 mAb crystalline suspension, obtained by bulk dialysis at pH 7.5, as discussed at Example 4. Anti-huIL-23p19 mAb 13B8-b was crystallized after dialysis against a solution comprising 10% 1,2 propanediol, 0.1 M HEPES (pH 7.5), and 20% PEG 400. The photomicrograph, at 400×magnification, was taken after 18 hours at 22° C. Particle sizes range from about 5-10 microns.

Bulk dialysis crystallization of anti-huIL-23p19 mAb 13B8-b at pH 7.5 was performed as follows. A solution of anti-huIL-23p19 mAb 13B8-b was prepared at 60 mg/ml in 10 mM sodium citrate (pH 5.5), and dialyzed in a Dispo-Dialyzer® (8K MW cutoff) membrane (Spectrum Laboratories, Inc., Rancho Dominguez, Calif., USA) against 10 ml of 10% 1,2 propanediol; 0.1 M HEPES (pH 7.5); and 20% PEG 400 for 18 hours at room temperature (22° C.). A photomicrograph of the resulting crystals is provided at FIG. 7. The crystalline suspension was recovered as described in Example 5 at 50% yield.

Figure 8:
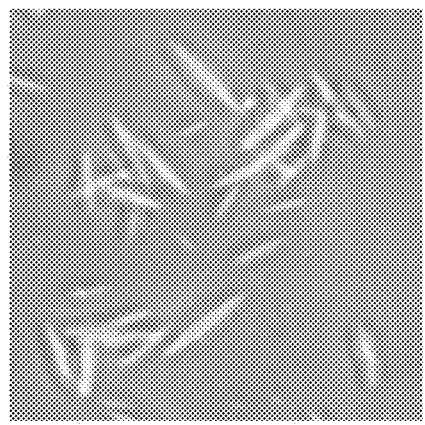
FIG. 8 is a photomicrograph of crystals within an anti-huIL-23p19 mAb crystalline suspension, obtained by bulk dialysis at pH 4.5, as discussed at Example 4. Anti-huIL-23p19 mAb 13B8-b was crystallized after dialysis against a solution comprising 14% PEG 300; 0.1 M sodium acetate (pH 4.5); and 0.2 M NaCl. The photomicrograph, at 400× magnification, was taken after 18 hours at 22° C. Particle sizes range from about 5-10 microns.

Bulk dialysis crystallization of anti-huIL-23p19 mAb 13B8-b was also performed at pH 4.5, as follows. A solution of anti-huIL-23p19 mAb 13B8-b was prepared at 60 mg/ml in 10 mM sodium citrate (pH 5.5), and dialyzed in a DispoDialyzer® (8K MW cutoff) membrane against 10 ml of 14% PEG 300; 0.1 M sodium acetate (pH 4.5); and 0.2 M NaCl for 18 hours at room temperature (22° C.). A photomicrograph of the resulting crystals is provided at FIG. 8. The crystalline suspension was recovered as described in Example 5 at 33% yield.

Example 5

Harvest of Crystalline Suspensions by Centrifugation

Crystalline anti-huIL-23p19 mAb 13B8-b is harvested from crystal suspensions as follows. The suspension is centrifuged in a Fisher microfuge at 5000 rpm for 5 minutes at room temperature. The mother liquor is removed by aspiration and the pellet is re-suspended in stabilizing solution (100 mM sodium citrate, pH 4.8, 25% PEG 400, 200 mM NaCl, 0.1% methyl paraben).

The crystalline suspension is again centrifuged for 5 minutes at 5,000 rpm, the supernatant (wash) is removed by aspiration and the pellet is resuspended in stabilizing solution. This wash step is repeated two more times. The resulting pellet is re-suspended in sterile stabilizing solution and stored at room temperature.

Example 6

Characterization of Crystalline Anti-huIL-23p19 mAb 13B8-b

Re-dissolved crystalline anti-huIL-23p19 mAb 13B8-b was characterized by SDS PAGE, dynamic light scattering (DLS), and ELISA, as follows.

A suspension of crystalline anti-huIL-23p19 mAb 13B8-b was centrifuged in a Fisher microfuge at 5000 rpm for 5 minutes at room temperature. The mother liquor was removed by aspiration and the pellet was re-suspended in stabilizing solution (100 mM sodium citrate, pH 4.8, 25% PEG 400, 200 mM NaCl, 0.1% methyl paraben). The suspension was again centrifuged for 5 minutes at 5,000 rpm, the supernatant (wash) is removed by aspiration and the pellet was resuspended in 10 mM sodium citrate (pH 5.5). The resulting solution was clarified by centrifugation, and the re-dissolved crystalline solution was used for characterization studies.

Figure 10:
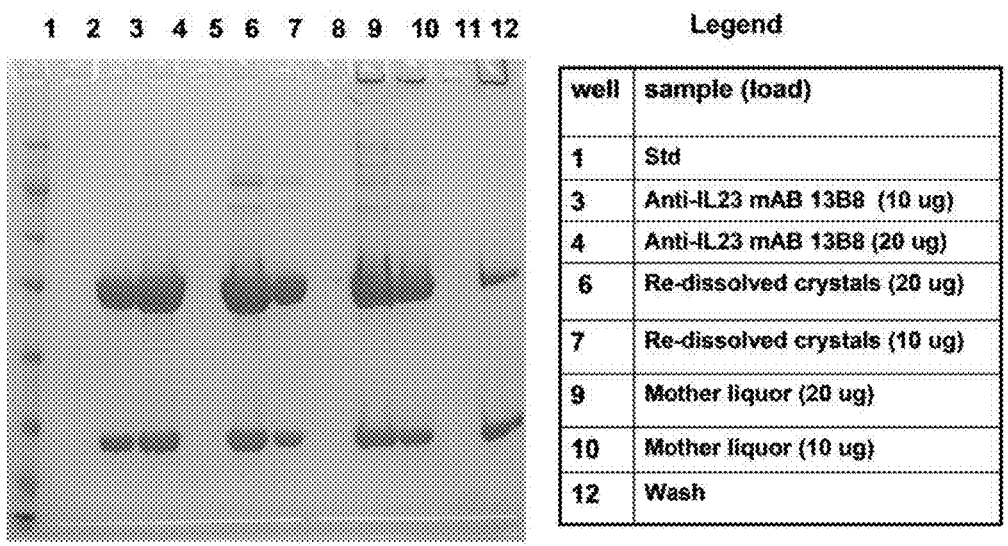
FIG. 10 presents a photograph of an SDS-PAGE gel comparing solution anti-huIL-23p19 mAb 13B8-b with the same material after it has been re-dissolved from the crystalline anti-huIL-23p19 mAb 13B8-b of the present invention. Details are provided at Example 6, and as indicated in the Legend. Lane 1 is MW markers, and lanes 2, 5, 8 and 11 are empty. Lanes 3 and 4 were loaded with 10 and 20 μg of solution antibody, respectively. Lanes 6 and 7 were loaded with 20 and 10 μg of re-dissolved crystalline antibody, respectively. Lanes 9 and 10 were loaded with 20 and 10 μg of the mother liquor aspirated from the crystalline suspension, and lane 12 was loaded with a portion of the wash.

Re-dissolved crystalline anti-huIL-23p19 mAb 13B8-b was compared to the original solution antibody by reducing SDS-PAGE, as illustrated by the gel photograph at FIG. 10. As used herein, "solution" anti-huIL-23p19 mAb 13B8-b refers to the same antibody as in the crystalline form of the invention (and is in fact its starting material), but it has never been crystallized. The re-dissolved crystalline anti-huIL-23p19 mAb 13B8-b, loaded in lanes 6 and 7 (20 and 10 μg, respectively), looks the same as the original solution form of the antibody, loaded in lanes 3 and 4 (10 and 20 μg, respectively).

Re-dissolved crystalline anti-huIL-23p19 mAb 13B8-b was also compared to the original solution antibody by dynamic light scattering. DLS can provide information about the distribution of species in solution, including the number of resolvable species, their size, and level of homogeneity from a single measurement. A DynaPro light scattering instrument (Wyatt Technologies, Santa Barbara, Calif., USA) was used to measure the aggregation state of anti-huIL-23p19 mAb 13B8-b in solution. The experimentally derived molecular weight for the re-dissolved crystal solution was judged to be monodisperse, and comparable to the anti IL-23p19 mAb starting material. See Table 3.

TABLE 3

| Anti-Hu-IL 23 mAB 13B8-b | Theoretical MW (kDa) | Experimental MW (kDa) | Polydispersity Index | Prediction |
|---|---|---|---|---|
| Solution | 150 | 90 | 16 | Monodisperse |
| Re-dissolved crystals | 150 | 45 | 15 | Monodisperse |

Re-dissolved crystalline anti-huIL-23p19 mAb 13B8-b was also compared to the original solution antibody by ELISA. Two different lots of each of solution and re-dissolved crystalline anti-huIL-23p19 mAb 13B8-b were tested for their ability to bind to IL-23. Human IL-23 was immobilized onto an ELISA plate, and serial dilutions of anti-huIL-23p19 mAb 13B8-b (solution or re-dissolved crystalline) were added to the wells. After the plates were washed, bound antibody was detected using an HRP-labeled anti-IgG antibody and a colorimetric substrate. Plates were read in a plate reader and the dose response curves were analyzed using a four-parameter logistic fit. At equilibrium, the EC50 of a saturation binding curve reflects the equilibrium binding dissociation constant ($K_D$), where a higher value represents lower affinity, and a lower value represents higher affinity, of the antibody for the ligand. The potency of the test sample is assessed by comparing binding curves of the test samples to a reference material by the ratio of the EC50's. Potency is expressed as percent of reference material, in this case, selected to be lot #1 of the solution form of anti-huIL-23p19 mAb 13B8-b. Results, provided at Table 4, indicate that re-dissolved crystalline anti-huIL-23p19 mAb 13B8-b exhibits comparable binding affinity to the original solution material.

TABLE 4

| Sample | EC50 (pM) | (std dev) | Relative potency (% Solution #1) |
|---|---|---|---|
| Solution #1 | 71 | ±15 | [100] |
| Solution #2 | 106 | ±50 | 67 |
| Re-dissolved Crystals #1 | 73 | ±10 | 97 |
| Re-Dissolved Crystals #2 | 116 | ±52 | 61 |

Example 7

X-Ray Diffraction Analysis of Anti-huIL-23p19 mAb 13B8-b Crystals

Anti-huIL-23p19 mAb 13B8-b crystals were characterized by X-ray diffraction as follows. Crystals were grown from a 60 mg/ml solution of anti-huIL-23p19 mAb 13B8-b in 10 mM sodium citrate (pH 5.5) by adding an equal volume of 20% PEG 400, 200 mM $Li_2SO_4$, 100 mM cacodylate (pH 6.4) as the precipitant solution. Crystallization was setup at 22° C. using a hanging drop technique. Crystals were harvested and cryo-protected using and 30% PEG 400, 200 mM $Li_2SO_4$, 100 mM cacodylate (pH 6.4). X-ray diffraction data were collected using synchrotron radiation at ID-17 (Argonne National Laboratory, Argonne, Ill., USA), and then processed and scaled using the HKL-2000 macromolecular crystallography software package (HKL Research, Inc., Charlottesville, Va., USA). A complete dataset was collected with a maximum resolution of 3.5 Å. Anti-huIL-23p19 mAb 13B8-b crystals belong to the I4 system with a=b=191.8 Å, c=105.9 Å (rounding to a=b=192 Å and c=106 Å), and alpha=beta=gamma=90 degrees.

Example 8

Use of Seeding in Crystallization of Anti-huIL-23p19 mAb 13B8-b

Figure 11A:
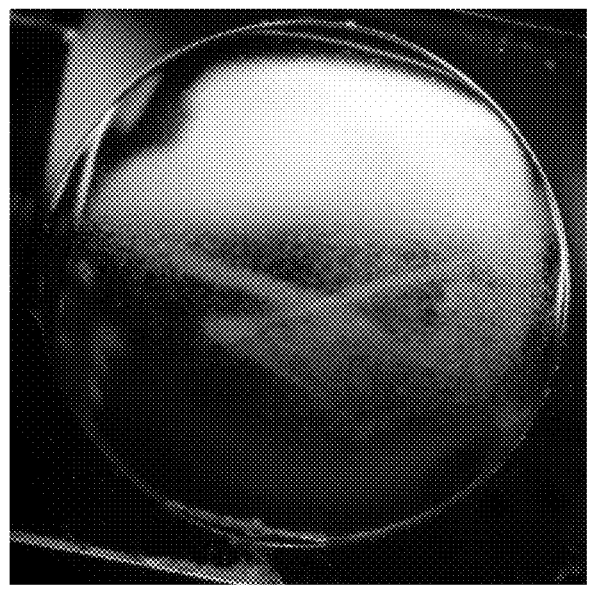
FIGS. 11A and 11B presents photographs of crystals obtained by seeding methods, as described in Example 8. Crystals were obtained by mixing equal volumes of anti-huIL-23p19 mAb 13B8-b in 10 mM sodium citrate (pH 5.5) with an equal volume of 27% PEG 400, 0.1 M sodium citrate (pH 4.83), 0.2 M NaCl at 22° C. Samples were incubated five days at 22° C. and then streaked with a pipette tip. Photographs were taken 24 hours after streaking (FIG. 11A), and again at 10 days after streaking (FIG. 11B).
Figure 11B:

Crystals of anti-huIL-23p19 mAb 13B8-b were prepared using a seeding protocol, as follows. A micro-bridge was inserted in each well of a VDX crystallization plate (Hampton Research, Aliso Viejo, Calif. USA). On each micro-bridge, 25 µl of a 60 mg/ml solution of anti-huIL-23p19 mAb 13B8-b in 10 mM sodium citrate (pH 5.5) was mixed with an equal volume of 27% PEG 400, 0.1 M sodium citrate (pH 4.83), 0.2 M NaCl at 22° C. The mixture was then incubated for 18 hours at room temperature (22° C.). After five days each experiment was streaked with a pipette tip. A photomicrograph of a representative drop after streaking is provided at FIG. 11A, and a photomicrograph of the final observed crystalline suspension before harvesting is provided at FIG. 11B. The crystalline suspension was harvested as described in Example 5 in 70% yield.

Example 9

Determining the Equilibrium Dissociation Constant ($K_D$) for Anti-Human IL-23p19 mAbs Using KinExA Technology Experiments to confirm that re-dissolved crystalline anti-huIL-23p19 mAb of the present invention retains binding affinity for human IL-23 may be performed as follows. The equilibrium dissociation constant ($K_D$) for re-dissolved crystalline anti human IL-23p19 antibodies, as well as solution anti-huIL-23p19 mAb (the starting material for making the crystalline antibody of the present invention), are determined using the KinExA 3000 instrument. Sapidyne Instruments Inc., Boise Id., USA KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg]$$

2. Antibody and antigen bind 1:1 and total antibody equals antigen-antibody complex plus free antibody.

3. Instrument signal is linearly related to free antibody concentration.

98 micron PMMA particles (Sapidyne, Cat No. 440198) are coated with biotinylated IL-23 according to Sapidyne "Protocol for coating PMMA particles with biotinylated ligands having short or nonexistent linker arms". In one embodiment of the experiment, biotinylated IL-23 comprises a complex of mouse IL-12p40 and human IL-23p19. EZ-link TFP PEO-biotin (Pierce, Cat. No. 21219) is used to make biotinylated IL-23 according to manufacturer's recommendations (Pierce bulletin 0874). All experimental procedures are done according to the KinExA 3000 manual.

Binding of re-dissolved crystalline anti-huIL-23p19 antibodies is assessed in a competition binding assay, in which antibodies are pre-incubated with non-linked (native) human IL-23 comprising two disulfide-linked chains, human p19 (SEQ ID NO: 13) and human p40 (GenBank Accession No. P29460), at a series of concentrations. The resulting samples, comprising a mixture of unbound antibodies and IL-23-bound antibodies, are then flowed over the rhIL-23 ("elastikine") PMMA particles described in the preceding paragraph. The amount of antibody captured by the PMMA particles is then detected using a fluorescently labeled secondary antibody.

The resulting $K_D$s for the starting material and the re-dissolved crystalline antibody are compared to determine whether the re-dissolved crystalline antibody retains sufficient binding affinity for human IL-23.

Example 10

Determining the Equilibrium Dissociation Constant ($K_D$) for Anti-Human IL-23p19 mAbs Using BIAcore Technology Additional experiments to confirm that re-dissolved crystalline anti-huIL-23p19 mAb of the present invention retains binding affinity for human IL-23 may be performed as follows. The equilibrium dissociation constant ($K_D$) for re-dissolved crystalline anti human IL-23 antibodies, as well as solution anti-huIL-23p19 mAb (the starting material for making the crystalline antibody of the present invention), are determined using surface plasmon resonance (SPR) methods, e.g. BIAcore technology. BIAcore Life Sciences, GE Healthcare Biosciences, Pittsburgh, Penna., USA. BIAcore determinations are performed essentially as described at Example 4 of commonly assigned U.S. Patent Application Publication No. 2007/0048315. Briefly, ligands (anti-huIL-23p19 mAbs) are immobilized on a BIAcore CM5 sensor chip using standard amine-coupling procedure. IL-23 is diluted in PBS to produce various concentrations. Kinetic constants for the various interactions are determined using BIAevaluation software 3.1. The $K_D$ is determined using the calculated dissociation and association rate constants.

The resulting $K_D$s for the starting material and the re-dissolved crystalline antibody are compared to determine whether the re-dissolved crystalline antibody retains sufficient binding affinity for human IL-23.

Example 11

Proliferation Bioassays for the Assessment of Neutralizing Anti-huIL-23p19 Antibodies Experiments to confirm that re-dissolved crystalline anti-huIL-23p19 mAb of the present invention retains the ability to neutralize human IL-23 may be performed by the application of short-term proliferation bioassays that employ cells that express recombinant IL-23 receptors, as follows. The IL-23R transfectant cell line (Ba/F3-2.2lo-hIL-23R) expresses both hIL-23R and hIL-12Rβ1, and is responsive to both human IL-23 and cynomolgus monkey IL-23. The transfectant Ba/F3-2.2lo cells proliferate in response to human IL-23 and the response can be inhibited by a neutralizing anti-huIL-23p19 antibody. An antibody is titrated against a concentration of IL-23 chosen within the linear region of the dose-response curve, near plateau and above EC50. Proliferation, or lack thereof, is measured by colorimetric means using Alamar Blue, a growth indicator dye based on detection of metabolic activity. The ability of an antibody to neutralize IL-23 is assessed by its IC50 value, i.e. the concentration of antibody that induces half-maximal inhibition of IL-23 proliferation.

Ba/F3 transfectants are maintained in RPMI-1640 medium, 10% fetal calf serum, 50 µM 2-mercaptoethanol, 2 mM L-Glutamine, 50 µg/ml penicillin-streptomycin, and 10 ng/ml mouse IL-3. Ba/F3 proliferation bioassays are performed in RPMI-1640 medium, 10% fetal calf serum, 50 µM 2-mercaptoethanol, 2 mM L-Glutamine, and 50 µg/ml penicillin-streptomycin.

Procedure

Assays are performed in 96-well flat bottom plates (Falcon 3072 or similar) in 150 µL per well. Anti-huIL-23p19 antibodies are pre-incubated with IL-23 for 30-60 min, followed by addition of cells and incubation for 40-48 hours. Alamar Blue (Biosource Cat #DAL1100) is added and allowed to develop for 5-12 hours. Absorbance is then read at 570 nm and 600 nm (VERSAmax Microplate Reader, Molecular Probes, Eugene, Oreg., USA), and an $OD_{570-600}$ is obtained.

Cells are used in a healthy growth state, generally at densities of $3-8 \times 10^5$/ml. Cells are counted, pelleted, washed twice in bioassay medium, and suspended to the appropriate density for plating. An IL-23 dose response is performed using serial 1:3 dilutions (25:50 µL in bioassay medium) of human IL-23. An IL-23 concentration of 3 ng/ml (50 pM) is selected for use in antibody assays. A neutralizing antibody dose response is also performed using serial 1:3 dilutions (25:50 µL in bioassay medium).

IC50 values are determined using GraphPad Prism® 3.0 software (Graphpad Software Inc., San Diego, Calif., USA), in which absorbance is plotted against cytokine or antibody concentration and IC50 values are determined using non-linear regression (curve fit) of sigmoidal dose-response.

The resulting IC50s for the starting material and the re-dissolved crystalline antibody are compared to determine whether the re-dissolved crystalline antibody retains the ability to neutralize human IL-23 at an acceptable level.

Example 12

Mouse Splenocyte Assay for IL-23 Based on IL-17 Production

The biological activity (neutralizing ability) of re-dissolved crystalline anti-huIL-23p19 antibodies of the present invention may also be assessed using the splenocyte assay essentially as described in Aggarwal et al. (2003) *J. Biol. Chem.* 278:1910 and Stumhofer et al. (2006) *Nature Immunol.* 7:937. The mouse splenocyte assay measures the activity of human IL-23 in a sample as a level of IL-17 production by murine splenocytes. The inhibitory activity of anti-huIL-23p19 antibodies is then assessed by determining the concentration of antibody necessary to reduce the IL-23 activity in a given sample by 50% (the IC50). The IC50 as measured by this assay is greater than or equal to the equilibrium dissociation binding constant ($K_D$), i.e. the $K_D$ may be equal to or lower than the IC50. As always, lower IC50 and $K_D$ values reflect higher activities and affinities.

Briefly, spleens are obtained from 8-12 wk old female C57BL/6J mice (Jackson Laboratories, Bar Harbor, Me., USA). Spleens are ground, pelleted twice, and filtered through a cell strainer (70 µm nylon). The recovered cells are cultured in 96-well plates ($4 \times 10^5$ cells/well) in the presence of human IL-23 (10 ng/ml, ~170 pM) and mouse-anti-CD3e antibodies (1 µg/ml) (BD Pharmingen, Franklin Lakes, N.J., USA), with or without the anti-huIL-23p19 antibody to be assayed. Anti-huIL-23p19 antibodies (re-dissolved from crystals or from solution) are added at 10 µg/ml and at a series of 3-fold dilutions. Cells are cultured for 72 hours, pelleted, and the supernatant is assayed for IL-17 levels by sandwich ELISA.

IL-17 ELISA is performed as follows. Plates are coated with a capture anti-IL-17 antibody (100 ng/well) overnight at 4° C., washed and blocked. Samples and standards are added and incubated for two hours at room temperature with shaking Plates are washed, and a biotinylated anti-IL-17 detection antibody (100 ng/well) is added and incubated for one hour at room temperature with shaking. The capture and detection antibodies are different antibodies that both bind to mouse IL-17 but do not cross-block. Plates are washed, and bound detection antibody is detected using streptavidin-HRP (horseradish peroxidase) and TMB (3,3',5,5'-tetramethylbenzidine). The plate is then read at 450-650 nm and the concentration of IL-17 in samples is calculated by comparison with standards. IC50s are calculated from the IL-17 levels.

The resulting IC50s for the starting material and the re-dissolved crystalline antibody are compared to determine whether the re-dissolved crystalline antibody retains the ability to neutralize human IL-23 at an acceptable level.

Table 5 provides a brief description of the sequences in the sequence listing.

TABLE 5

| SEQ ID NO: | Description |
| --- | --- |
| 1 | 13B8 HC-a |
| 2 | 13B8 HC-b |
| 3 | 13B8 HC-c |
| 4 | 13B8 LC |
| 5 | 13B8 CDRH1 |
| 6 | 13B8 CDRH2-a |
| 7 | 13B8 CDRH2-b |
| 8 | 13B8 CDRH2-c |
| 9 | 13B8 CDRH3 |
| 10 | 13B8 CDRL1 |
| 11 | 13B8 CDRL2 |
| 12 | 13B8 CDRL3 |
| 13 | human IL-23p19 |
| 14 | 13B8-b HC DNA |
| 15 | 13B8 LC DNA |
| 16 | ustekinumab CDRH1 |
| 17 | ustekinumab CDRH2 |
| 18 | ustekinumab CDRH3 |
| 19 | ustekinumab CDRL1 |
| 20 | ustekinumab CDRL2 |
| 21 | ustekinumab CDRL3 |
| 22 | ustekinumab $V_H$ |
| 23 | ustekinumab $V_L$ |
| 24 | ustekinumab HC |
| 25 | ustekinumab LC |
| 26 | briakinumab CDRH1 |
| 27 | briakinumab CDRH2 |
| 28 | briakinumab CDRH3 |
| 29 | briakinumab CDRL1 |
| 30 | briakinumab CDRL2 |
| 31 | briakinumab CDRL3 |
| 32 | briakinumab $V_H$ |
| 33 | briakinumab $V_L$ |
| 34 | briakinumab HC |
| 35 | briakinumab LC |
| 36 | guselkumab CDRH1 |
| 37 | guselkumab CDRH2 |
| 38 | guselkumab CDRH3 |
| 39 | guselkumab CDRL1 |
| 40 | guselkumab CDRL2 |
| 41 | guselkumab CDRL3 |
| 42 | guselkumab $V_H$ |
| 43 | guselkumab $V_L$ |
| 44 | guselkumab HC |
| 45 | guselkumab LC |

What is claimed is:

1. A crystalline anti-human IL-23p19 antibody comprising:
   a) an antibody light chain variable domain comprising CDRL1, CDRL2 and CDRL3, wherein:
      i) CDRL1 comprises the sequence of SEQ ID NO: 10;
      ii) CDRL2 comprises the sequence of SEQ ID NO: 11; and
      iii) CDRL3 comprises the sequence of SEQ ID NO: 12; and
   b) an antibody heavy chain variable domain comprising CDRH1, CDRH2 and CDRH3, wherein:
      i) CDRH1 comprises the sequence of SEQ ID NO: 5;
      ii) CDRH2 comprises a sequence selected from the group consisting of SEQ ID NO: 7; and
      iii) CDRH3 comprises the sequence of SEQ ID NO: 9;
wherein the crystalline antibody neutralizes human IL-23 and wherein the crystalline anti-human IL-23p19 antibody is characterized by unit cell dimensions a=b=192Å, c=106Å, $\alpha=\beta=\gamma=90°$ and in space group I4.

2. The crystalline anti-human IL-23p19 antibody of claim 1 comprising crystalline particles with an average particle size between five and 200 microns.

3. A suspension of the crystalline anti-human IL-23p19 antibody of claim 1 in which the antibody is at a concentration of at least 150 mg/ml.

4. The suspension of claim 3 in which the viscosity of the suspension is less than about half the viscosity of a solution formulation of the same antibody at the same concentration.

5. The crystalline anti-human IL-23p19 antibody of claim 1 comprising:
   a) an antibody light chain variable domain comprising residues 1-108 of SEQ ID NO: 4; and
   b) an antibody heavy chain variable domain comprising residues 1-116 of SEQ ID NO: 2.

6. The crystalline anti-human IL-23p19 antibody of claim 1 comprising an antibody light chain and an antibody heavy chain, wherein:
   a) the antibody light chain comprises the sequence of SEQ ID NO: 4; and
   b) the antibody heavy chain comprises the sequence of SEQ ID NO: 2.

7. The crystalline anti-human IL-23p19 antibody of claim 1, further comprising a heavy chain constant region comprising a γ1 human heavy chain constant region.

8. A pharmaceutical composition comprising the crystalline anti-human IL-23p19 antibody of claim 1 in combination with a pharmaceutically acceptable carrier or diluent.

* * * * *